United States Patent
Lazar et al.

(10) Patent No.: US 10,314,518 B2
(45) Date of Patent: Jun. 11, 2019

(54) SYSTEM AND METHODS FOR THE MEASUREMENT OF LUNG VOLUMES

(75) Inventors: Avi Lazar, RaAnana (IL); Mark Gaides, Ashdod (IL); Betsalel Rechav, Nes Ziona (IL); Ori Adam, Rechovot (IL); Yehoshua Sheinman, Ra'Anana (IL)

(73) Assignee: PULMONE ADVANCED MEDICAL DEVICES, LTD., Ra'Anana (IL)

( * ) Notice: Subject to any disclaimer, the term of this patent is extended or adjusted under 35 U.S.C. 154(b) by 281 days.

(21) Appl. No.: 12/670,661

(22) PCT Filed: Jul. 27, 2008
(Under 37 CFR 1.47)

(86) PCT No.: PCT/IL2008/001031
§ 371 (c)(1),
(2), (4) Date: Aug. 23, 2010

(87) PCT Pub. No.: WO2009/013755
PCT Pub. Date: Jan. 29, 2009

(65) Prior Publication Data
US 2011/0201958 A1 Aug. 18, 2011

Related U.S. Application Data

(60) Provisional application No. 60/951,998, filed on Jul. 26, 2007.

(51) Int. Cl.
*A61B 5/087* (2006.01)
*A61B 5/091* (2006.01)
*A61B 5/097* (2006.01)

(52) U.S. Cl.
CPC .............. *A61B 5/097* (2013.01); *A61B 5/091* (2013.01); *A61B 5/087* (2013.01)

(58) Field of Classification Search
CPC ....... A61B 5/087; A61B 5/091; A61B 5/0806; A61B 5/085
(Continued)

(56) References Cited

U.S. PATENT DOCUMENTS 3,100,620 A   8/1963   Kates
4,307,730 A   12/1981  Korn
(Continued)

FOREIGN PATENT DOCUMENTS

WO      2006/102086 A1    9/2006
WO   WO 2009/013755       1/2009

OTHER PUBLICATIONS

Notification of Transmittal of the International Search Report and the Written Opinion of the International Searching Authority, or Declaration (1 page); International Search Report (3 pages); and Written Opinion of the International Searching Authority (6 pages), dated Dec. 14, 2011, for related international application PCT/IL11/00533.
(Continued)

*Primary Examiner* — Tiffany Weston
(74) *Attorney, Agent, or Firm* — Buckley, Maschoff & Talwalkar LLC

(57) ABSTRACT

A system and method for determining FRC, TGV, TLC and RV includes a hand-held unit with a shutter assembly designed to minimize measured air displacement due to shuttering. Measurements of flow and pressure are used to derive the lung parameters.

43 Claims, 13 Drawing Sheets

(58) Field of Classification Search
USPC .................................................. 600/529–543
See application file for complete search history.

(56) References Cited

U.S. PATENT DOCUMENTS

| | | | |
|---|---|---|---|
| 4,930,498 A | 6/1990 | Hayek | |
| 5,233,998 A | 8/1993 | Chowienczyk et al. | |
| 5,261,397 A * | 11/1993 | Grunstein | A61B 5/085 128/204.18 |
| 5,522,397 A * | 6/1996 | Vermaak | 600/533 |
| 5,857,459 A * | 1/1999 | Snow | A61B 5/091 128/204.21 |
| 5,876,352 A * | 3/1999 | Weismann | A61B 5/085 600/529 |
| 6,066,101 A | 5/2000 | Johnson et al. | |
| 6,183,423 B1 | 2/2001 | Gaumond et al. | |
| 6,723,055 B2 | 4/2004 | Hoffman | |
| 2001/0037071 A1 * | 11/2001 | Lingo et al. | 600/538 |
| 2004/0186390 A1 | 9/2004 | Ross et al. | |
| 2004/0249300 A1 * | 12/2004 | Miller | 600/532 |
| 2006/0264772 A1 | 11/2006 | Aljuri et al. | |
| 2006/0276807 A1 | 12/2006 | Keast et al. | |
| 2007/0135724 A1 | 6/2007 | Ujhazy et al. | |
| 2007/0142742 A1 | 6/2007 | Aljuri et al. | |
| 2007/0185406 A1 | 8/2007 | Goldman | |
| 2008/0077033 A1 | 3/2008 | Figueiredo et al. | |

OTHER PUBLICATIONS

Authorized officer, Simin Baharlou, International Preliminary Report on Patentability, International Application No. PCT/IL11/00533, dated Jan. 17, 2013, 8 pages.
Supplemental European Search Report; Application No. 08789707.0 dated Jan. 31, 2013, 7 pages.
International Preliminary Report and Written Opinion; Application No. PCT/IL2011/000533, dated Jan. 8, 2013, 7 pages.
International Preliminary Report and Written Opinion; Application No. PCT/IL2008/001031, dated Jan. 26, 2010, 7 pages.
"Extended European Search Report", European patent Office, Jun. 2, 2017 (Feb. 6, 2017), for European Application No. 14822765.5-1657, 7pgs.

* cited by examiner

SYSTEM AND METHODS FOR THE MEASUREMENT OF LUNG VOLUMES

RELATED APPLICATIONS

This Application is a National Phase of PCT Patent Application No. PCT/IL2008/001031 having International filing date of Jul. 27, 2008, which claims the benefit of U.S. Provisional Patent Application No. 60/951,998 filed on Jul. 26, 2007. The contents of the above Applications are all incorporated herein by reference.

FIELD OF THE INVENTION

The present invention relates to measurement of respiratory parameters and, more particularly to measurement of FRC, TGV, TLC and RV.

BACKGROUND OF THE INVENTION

Absolute lung volume is a key parameter in pulmonary physiology and diagnosis but is not easy to measure in the live individual. It is relatively straightforward to measure the volume of air which is exhaled from a subject's mouth but at the end of complete exhalation, a significant amount of air is always left in the lungs because the mechanical properties of the lungs and chest wall, including the ribs, do not allow the lungs to collapse completely. The gas left in the lungs at the end of a complete exhalation is termed the Residual Volume (RV) which may be significantly increased in disease. The total volume of gas in the lungs at the end of a maximal inspiration is termed the Total Lung Capacity (TLC) which includes the RV plus the maximum amount of gas which can be inhaled or exhaled and which is termed the Vital Capacity (VC). However, during normal breathing the subject does not empty the lungs down to RV nor inflate them to TLC. The amount of gas in the lungs at the end of a normal breath, as distinct from a complete exhalation, is termed the Functional Residual Capacity (FRC) or Thoracic Gas Volume (TGV), depending upon the manner in which it is measured. For simplicity when this volume is measured by inert gas dilution techniques it will be termed FRC and when measured by barometric techniques involving gas compression as in this application it will be termed TGV.

In order to determine the total volumes of gas in the lungs at TLC, TGV or RV, indirect methods must be used since it is impossible to completely exhale all the gas from the lungs. There are two basic techniques currently available, gas dilution and whole body plethysmography (a barometric method). Gas dilution involves the dilution of a known concentration and volume of inert gas by the gas in the lungs of the subjects and is critically dependent on complete mixing of the marker gas and lung gas. In subjects with poor gas mixing due to disease, this technique is very inaccurate and generally underestimates the true FRC. In the whole body plethysmograph, the subject makes respiratory efforts against an obstruction within a gas tight chamber and the changes in pressure on the lung side of the obstruction can be related to the changes in pressure in the chamber through Boyle's law to calculate TGV. This method accurately measures TGV even in sick subjects but requires complicated and expensive equipment and is difficult to perform.

Once FRC (gas dilution), or TGV (whole body plethysmograph), is calculated, the measurement by spirometry of the extra volume of gas which can be exhaled from the end of a normal exhalation (Expiratory Reserve Volume, ERV) and the extra volume which can be inhaled from the end of a normal exhalation (Inspiratory Capacity, IC) allows the calculation of TLC and RV.

These three important indicators (TLC, RV and FRC or TGV) are mutually connected through the following formulas: RV=FRC−ERV and TLC=FRC+IC and, TLC=RV+ERV+IC=RV+VC.

If FRC is determined by gas dilution and TGV by a barometric method, then the difference between them (TGV minus FRC) is a measure, albeit approximate, of the volume of poorly ventilated or 'trapped gas' in the lungs.

In healthy subjects TGV and FRC should be virtually identical as there is little or no trapped gas, hence, for all practical matters, the term TGV shall apply for FRC as well. In summary, determination of TLC, TGV and RV is central to the complete evaluation of lung function.

At the present time, FRC is measured by two gas-based techniques: the rebreathing of an inert gas, such as helium, in a closed circuit or the wash in or out of an inert marker gas, which can be the nitrogen, normally present in the lung. Both techniques have been used for several decades and are known to have several shortcomings, e.g., they are complex, hard to operate, moderately expensive, unreliable for the measurement of FRC in patients with poor gas mixing due to disease, and the tests are lengthy and uncomfortable for the subjects.

Body plethysmograph devices for determination of TGV are disclosed, for example, in U.S. Pat. No. 6,113,550 to Wilson, and have been known and used since at least 1955. Other devices, which include the use of impedance belts have been disclosed as well, for example, in U.S. Pat. No. 5,857,459. In both types of devices, the plethysmograph chamber or the impedance belts are designed so that the volume in the lungs can be calculated directly, so as to provide reliable measurement parameters for calculation of TGV. However, these methods for measuring TGV are all less than optimal, requiring a sealed chamber in which the subject sits, or external belts which have been shown not to provide reliable results and which may be bulky, expensive and inconvenient to operate, and require full cooperation of the subject during the measurement maneuvers to obtain meaningful results.

Hand held devices for measurement of certain lung parameters, such as spirometers, are known in the art. However, spirometers are not designed to measure internal volume. Other hand held devices known in the art include devices which have been used to determine airway resistance. Such devices use a shutter mechanism for blocking and opening of airways. For example, U.S. Pat. No. 5,233,998 to Chowienczyk discloses an apparatus with an interrupting valve for interrupting the flow of air through a bore. However, since this device is designed to measure resistance to air flow rather than lung volume, the shutter speeds may be relatively slow, and relative air displacement may occur.

The importance and need for a new, accurate, and easy to use method and device to measure TGV have been clearly stated in the ATS (American Thoracic Society)/NHLBI (U.S. National Heart, Lung and Blood Institute) Consensus Statement of Measurement of Lung Volumes in Humans, Clausen and Wagner et al., Nov. 12, 2003 (the Consensus Statement), page 6: "Systems will be available in the future which through new technology will offer potential advantages (e.g., ease of use, rapidity of testing, improved accuracy) over the methodology recommended in this document (i.e., nitrogen wash-out, helium gas dilution and body plethysmography). The ATS and the ERS (European Respiratory Society) encourage such innovation. However, it is the responsibility of the manufacturers to demonstrate that the lung volumes reported by new technology do not differ substantially from those obtained by the standard techniques; such comparisons must be made using subjects with varying severities of obstructive and restrictive lung disease as well as healthy subjects."

It is thus an object of the present invention to provide systems and methods for measurement of TGV without the need for external belts or chambers and which can provide accurate measurements which are up to the standards of the currently used systems.

SUMMARY OF THE INVENTION

In accordance with embodiments of the present invention, there is provided a method of calculating lung parameters. The method includes providing a system for measuring volume changes in the lungs, the system including a respiration module for inhalation or exhalation, commanding the system to occlude air flow within the respiration module during an inhalation or exhalation, obtaining a flow curve and a pressure curve during the occlusion, calculating an instantaneous volume in the lungs during the occlusion based on parameters of the flow curve and the pressure curve, and calculating a lung volume parameter based on the calculated volume.

In some embodiments, the occlusion of air flow may occur for less than 0.25 seconds and more preferably, for less than 5 ms and even more preferably for less than 2 ms. Calculating the instantaneous volume in the lungs may include determining a first pressure at a first point along the pressure curve, determining a second pressure at a second point along the pressure curve, calculating a pressure change by calculating a difference between the first pressure and the second pressure, determining a first flow point along the flow curve, determining a second flow point along the flow curve, calculating a volume change by integrating the flow curve from the first flow point to the second flow point, and calculating the instantaneous volume from the pressure change and the volume change. In some embodiments, the first point along the pressure curve is approximately at a start of the occlusion of air flow and the second point along the pressure curve is approximately at an end of the occlusion of air flow. In some embodiments, the first flow point is a first point which reaches a baseline flow value following the occlusion of air flow and the second flow point is a second point which reaches the baseline flow value following the first flow point. In other embodiments, the first flow point is a first point which reaches a baseline flow value following the occlusion of air flow and the second flow point is substantially equivalent in time to a point along the pressure curve of a local minimum of pressure.

In some embodiments, calculating the instantaneous volume in the lungs includes calculating a rate of pressure change, determining a baseline flow prior to shutter occlusion, and calculating the instantaneous volume based on the rate of pressure change and the baseline flow.

Embodiments of the present invention further include calculating TGV, FRC, RV and/or TLC based on the calculated instantaneous volume.

There is provided, in accordance with additional embodiments of the present invention, a system for determining respiratory parameters. The system includes a respiration module having a housing with a first end, a second end, and a body connecting the first end and the second end, the body forming a cavity for air flow in a first direction, a shutter assembly having a movable portion positioned within the cavity, the movable portion movable in a second direction which is substantially orthogonal to the first direction. The movable portion is configured to block and allow air flow. The system further includes a pressure measurement component positioned within the cavity for measuring pressure, and an air flow measurement component positioned within the cavity for measuring air flow in said cavity, and a control unit configured to receive pressure data from the pressure measurement component and flow data from the air flow measurement component.

There is provided, in accordance with additional embodiments of the present invention, a system for determining respiratory parameters. The system includes a respiration module having a housing with a first end, a second end, and a body connecting the first end and the second end, the body forming a cavity for air flow in a first direction, the cavity having a pre-shutter cavity component and a post-shutter cavity component, and a shutter assembly with a movable portion positioned within the cavity. The movable portion is configured to move in a second direction such that an opening is created for movement of air flow through the post-shutter cavity component of the cavity, the post-shutter cavity component having a flow area for movement of air flow past said movable portion, wherein a cross-sectional surface area of the movable portion in the second direction is smaller than the flow area of the post-shutter cavity component. The respiration module further includes a pressure measurement component positioned within the cavity for measuring pressure in the cavity, and an air flow measurement component positioned within the cavity for measuring air flow in the cavity. The system further includes a control unit configured to receive pressure data from the pressure measurement component and air flow data from the air flow measurement component.

There is provided, in accordance with yet additional embodiments of the present invention, a hand-held device for measurement of respiratory parameters. The device includes a housing having a first end, a second end, and a body connecting the first end and second end, the body forming a cavity for air flow. The device further includes a shutter assembly with a movable portion positioned within the cavity, wherein a cycle is defined as a single closing and a single opening of the cavity to air flow via the movable portion, and wherein the movable portion is configured to move at a speed of at least 5 ms per cycle. The device further includes a pressure measurement component positioned within the cavity for measurement of pressure within the cavity; and an air flow measurement component positioned within the cavity for measurement of a flow parameter within the cavity.

In accordance with further features, the respiration module may be a hand-held device that is positionable at a mouth of a user.

In some embodiments, the shutter assembly includes a housing having at least one wall defining a chamber, and an air outlet in the wall, wherein the movable portion includes a sealing portion. In a first configuration, the sealing portion abuts a portion of the chamber thereby blocking air flow through the chamber, and in a second configuration the sealing portion does not abut the portion of the chamber, thereby allowing air flow through the chamber and out through the air outlet.

In other embodiments, the shutter assembly includes a housing defining a chamber which is substantially cylindrical, a disk having edges and at least one opening, the disk positioned within the chamber such that air is prevented from flowing around its edges, wherein the movable portion is a rotatable shutter for opening and closing of the one opening. The disk may be movable in a direction opposite to a direction of movement of the rotatable shutter.

In yet additional embodiments, the shutter mechanism includes an outer cylinder with an outer slit along at least a portion of a length of thereof, and the movable portion includes an inner rotatable cylinder having an inner slit along at least a portion of a length thereof. The inner rotatable cylinder is positioned within the outer cylinder such that air is prevented from flowing between the outer cylinder and the inner rotatable cylinder, and wherein when the outer slit and the inner slit are aligned, the opening for said movement of air flow is created. The outer cylinder may be movable in a direction which is opposite to a direction of movement of said inner rotatable cylinder.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The above and further advantages of the present invention may be better understood by referring to the following description in conjunction with the accompanying drawings in which.

Figure 1:
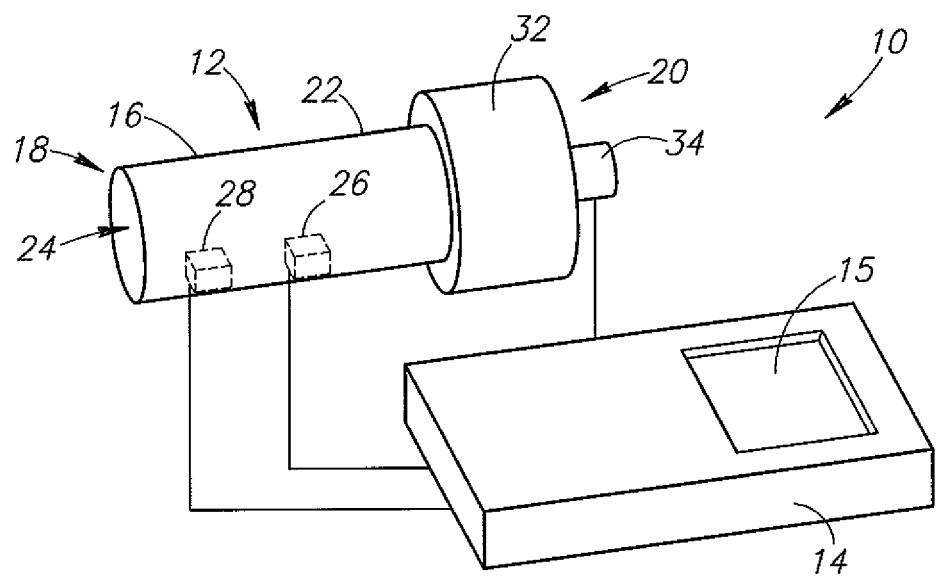
FIG. 1 is a schematic illustration of a system for measurement of respiration parameters, in accordance with embodiments of the present invention.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of the present invention. It will be understood by those of ordinary skill in the art that the present invention may be practiced without these specific details. In other instances, well-known methods, procedures, components and structures may not have been described in detail so as not to obscure the present invention.

The present invention is directed to a system and methods for determination of lung parameters, and more particularly, determination of Functional Residual Capacity (FRC) Thoracic Gas Volume (TGV), Total Lung Capacity (TLC) and Residual Volume (RV). The system and methods of the present application are designed to directly measure volume in the lungs with a handheld device, without the use of external chambers or belts. The principles and operation of a system and methods according to the present invention may be better understood with reference to the drawings and accompanying descriptions.

Before explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Reference is now made to FIG. 1, which is a schematic illustration of a system 10 for measurement of respiration parameters, in accordance with embodiments of the present invention. System 10 includes a respiration module 12 and a control unit 14. Respiration module 12 is typically a hand-held device that is positionable at a mouth of a user, and is used for inhalation and/or exhalation of air for the purposes of measuring respiration parameters of the user. Respiration module 12 includes a housing 16 having a first end 18 and a second end 20, and a housing body 22 extending from first end 18 to second end 20 and defining a cavity 24 therethrough. Respiration module 12 includes a shutter assembly 32 which can open or close to allow or prevent air flow therethrough and which is controlled by a motor 34. Respiration module may be designed to introduce air flow resistance of less than 1.5 cm $H_2O$/Liter/sec, in accordance with ATS (American Thoracic Society) guidelines for respiratory devices.

Housing 16 may further include at least one pressure measurement component 26 and at least one air flow measurement component 28. Pressure measurement component 26 may be any suitable manometer or sensor for the measurement of absolute pressure with a data rate of at least 500 Hz; and preferably at a data rate of at least 1000 Hz. Such pressure sensors are readily available and may be acquired, for example, from Honeywell Catalog #40PC001B1A. Air flow measurement component 28 may be fabricated for example from an air flow resistive means and a differential pressure manometer, or alternatively from a Pitot tube and a differential pressure manometer. The differential pressure manometer may be any suitable sensor with a data rate of at least 500 Hz; and preferably at a data rate of at least 1000 Hz. Such differential pressure manometers are readily available and may be acquired (for example, from Honeywell Catalog #DC002NDR4. Control unit 14 is in electrical communication with pressure measurement component 26, air flow measurement component 28, and motor 34, which is used for opening and closing of a shutter mechanism, as will be described further hereinbelow.

Figure 2:
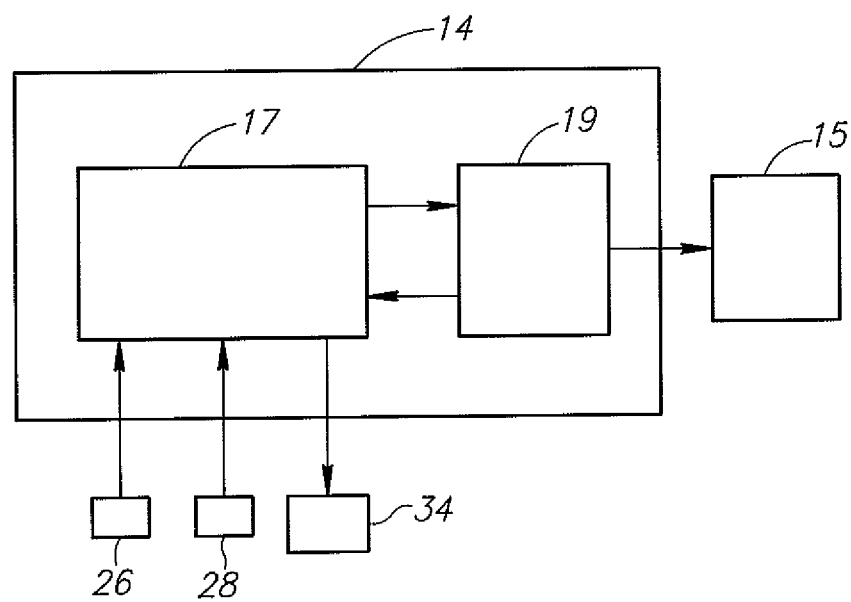
FIG. 2 is a block diagram illustration of a control unit of the system of FIG. 1.

Reference is now made to FIG. 2, which is a block diagram illustration of control unit 14. Control unit 14 may include a converter 17 which converts analog data received from pressure measurement component 26 and air flow measurement component 28 into digital format at a rate of at least once every 2 milliseconds (ms), and preferably at a rate at least once every 1 ms. Converter 17 converts digital signals into commands to motor 34 for shutter assembly 32 to close and to open. Control unit 14 further includes a microprocessor 19 which is programmed to: (a) read digital data of pressure and flow received from the converter 17 in accordance with real-time recording, at a rate commensurate with the converter rate for each data channel and translate this digital data into pressure and flow appropriate units and store them; (b) generate signals which are sent through converter 17 to motor 34 to command the shutter to close or to open, and (c) process above mentioned flow and pressure data in accordance with real time recording, to calculate lung volume and specifically calculate TGV, TLC and RV. Microprocessor 19 also manages a Man-Machine Interface (MMI) that accepts operation commands from an operator and displays results. Control unit 14 may further include a display 15 for displaying the resulting values. Control unit 14 may further include a keyboard to enter subject's personal and medical information and to select desired operational modes such as shuttering duration, timing, manual versus automatic operation, calibration procedures, etc.

Figure 3:
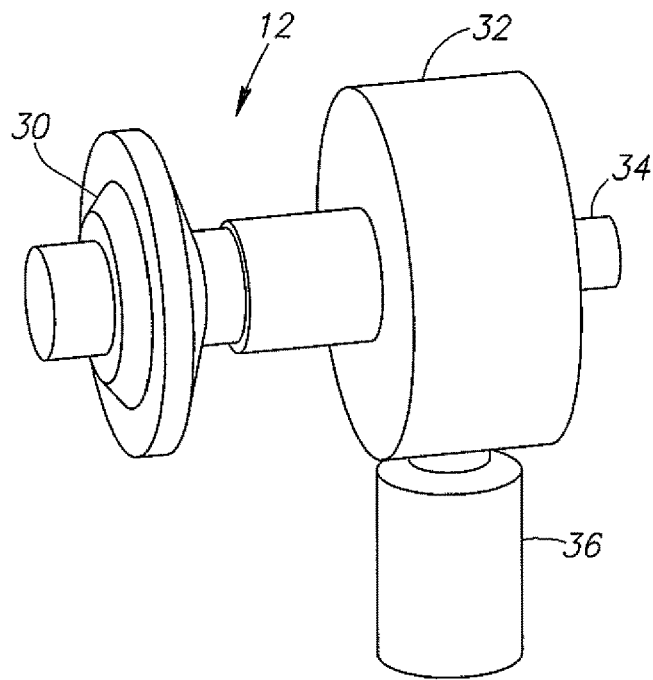
FIG. 3 is a perspective view illustration of a respiration module of the system of FIG. 1, in accordance with one embodiment of the present invention.

Reference is now made to FIG. 3, which is a perspective view illustration of respiration module 12 in accordance with one embodiment of the present invention. Respiration module 12 includes a mouthpiece 30 for placement into a mouth of a user, a shutter assembly 32 attached to (but which may be removable from) mouthpiece 30, a motor 34 for controlling movements of shutter assembly 32, and a flow meter tube 36, which is the air flow resistive means used to calculate air flow parameters. Mouthpiece 30 may be any suitable mouthpiece such as, for example, those available from A-M Systems, Inc. catalog number 156300. Shutter assembly 32 may have several different configurations, some of which will be described in greater detail. Shutter assembly 32 is designed specifically to minimize air displacement during opening and closing thereof. Motor 34 may be any suitable motor such as, for example, a standard solenoid. Alternatively, motor 34 may be any electronically, pneumatically, hydraulically or otherwise operated motor. Finally, flow meter tube 36 is a section of respiration module 12 which is distal to shutter assembly 32. In the present embodiment, flow meter tube 36 is distal to shutter assembly 32 so that measurement of air flow can be taken downstream of the open or closed shutter. However, flow meter tube 36 may also be positioned adjacent to pressure measurement component 26. Flow meter tube 36 may be calibrated in accordance with known methods so as to account for variations in density due to differences in room temperature and body temperature.

Figure 4:
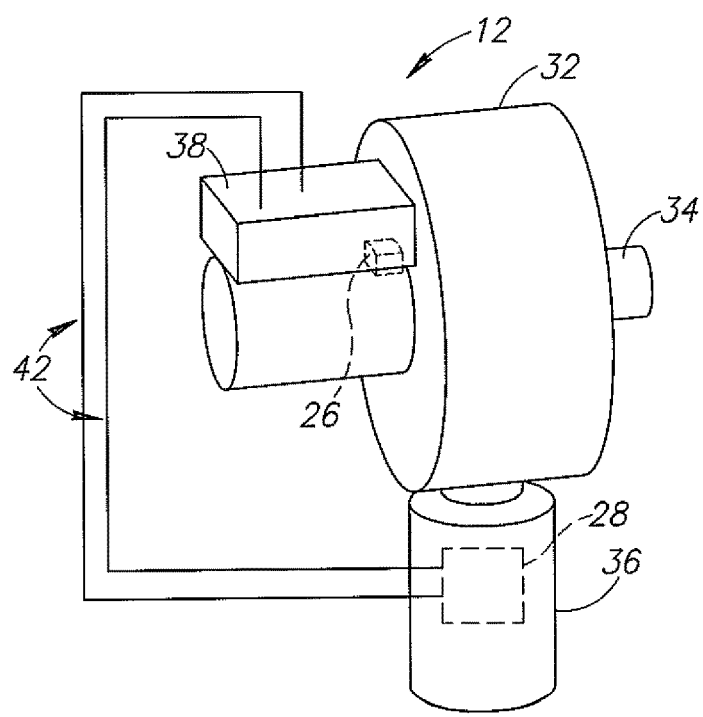
FIG. 4 is a schematic illustration showing the respiration module of FIG. 3 with the addition of electronic components.

Reference is now made to FIG. 4 which is a schematic illustration showing the respiration module 12 of FIG. 3 with the addition of electronic components. An electronics module 38 may be positioned on or next to shutter assembly 32. Electronics module 38 is configured to receive data from pressure and flow measurements and to send the received data to control unit 14 for processing. In some embodiments, control unit 14 is attached to respiration module 12 (and more particularly, to electronics module 38) via wires. In other embodiments, wireless connections may be employed. In the embodiment shown in FIG. 4, pressure measurement component 26 is a pressure sensor positioned in close proximity to mouthpiece 30 and shutter assembly 32 and is within or in direct contact with electronics module 38, and air flow measurement component 28 is a flow meter tube 36 connected via tubes 42 to a differential pressure sensor positioned on or within electronics module 38. Thus, the pressure sensor receives an air pressure signal through an air pipe from shutter assembly 32 from a point between mouthpiece 30 and shutter assembly 32. The pressure sensor outputs an electrical signal proportional to the air pressure in the pipe (relative to the surrounding atmospheric pressure). The differential pressure sensor accepts two air pipes from flow meter tube 36. The differential pressure sensor outputs an electronic signal proportional to the difference in pressure between the two pipes, which may be converted into a flow signal. It should be readily apparent that the invention is not limited to the embodiment shown herein and that in some embodiments, electronics module 38 may be positioned in a different location.

Shutter assembly 32 is used for breaking a stream of inhaled or exhaled air, located within cavity 24. Shutter assembly 32 is configured to operate quietly so as not to create any reflexes or undesired responses by the subject, thereby avoiding inaccuracies of measurement. More importantly, shutter assembly 32 is configured to operate quickly, both in terms of its shutting speed (i.e., the time it takes for the shutter to go from an open state to a closed state) and in terms of its shutting duration (i.e., the period of time for which the shutter is closed). The shutting speed is in some embodiments less than 10 ms, preferably less than 5 ms, and more preferably less than 2 ms. The shutting duration is in some embodiments less than 2 seconds and preferably less than 100 ms. This fast paced shutting speed and shutting duration are key features in the present invention to provide the accuracy and reliability of the measurement of TGV, TLC and RV. The need for high speed operation of shutter assembly 32 and high rate of data acquisition (as described above with reference to control unit 14) results from the typical response time of the lungs to abrupt occlusion of the airways while breathing. The response time of the lungs of a human being is in the order of ms to tens of ms, and accurate recording of the details of the response of the lungs to such abrupt occlusion is essential for accurate calculation of the internal volume of the lungs.

Figure 5A:
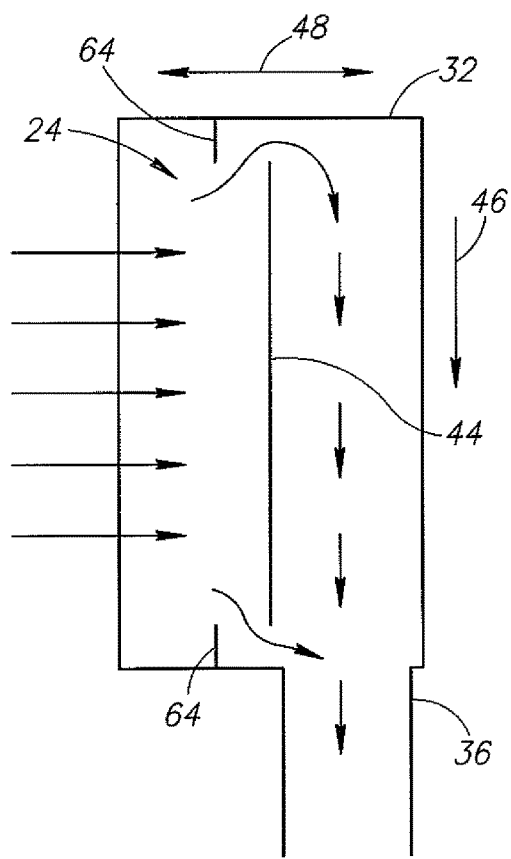
FIGS. 5A and 5B are schematic illustrations showing a movable portion positioned within a shutter assembly which is configured to move back and forth, shown in an open configuration and a sealed configuration, respectively.
Figure 5B:
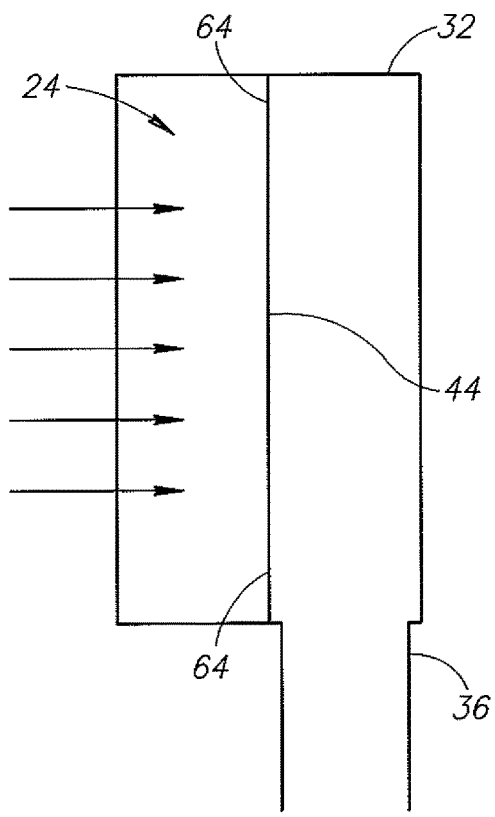

In addition to high speed, shutter assembly 32 is also configured to perform occlusion of cavity 24 with minimum, and preferably without any, displacement of air that may be recorded by the pressure sensor or the flow sensor. In order to provide rapid shutter movement with minimal air displacement, shutter assembly 32, as well as other embodiments of shutter assembly in accordance with the present invention, is designed so that the open/close movement of the shutter is substantially orthogonal to the direction of air flow being measured. Thus, in one embodiment, as shown in FIGS. 5A and 5B, a movable portion 44 is positioned within shutter assembly 32 and is configured to move back and forth in a first direction, as shown by arrow 48. A fixed portion 64 may be present as well, wherein when movable portion 44 is in an open position, movable portion 44 does not contact fixed portion 64 so as to allow for air flow, and when movable portion is in a closed position, movable portion 44 is in contact with fixed portion 64 so as to seal any air flow pathways. Air flow which enters shutter assembly 32 is configured to move in a direction which is substantially orthogonal to the movement of movable portion 44, as shown by arrow 46. In FIG. 5A, shutter assembly 32 is shown in an open configuration, wherein air flow is possible; in FIG. 5B, shutter assembly 32 is shown in a closed configuration, wherein air flow is stopped due to the movement of movable portion 44 and contact of movable portion 44 with fixed portion 64. A more detailed example of this type of configuration will be described hereinbelow.

Figure 6:
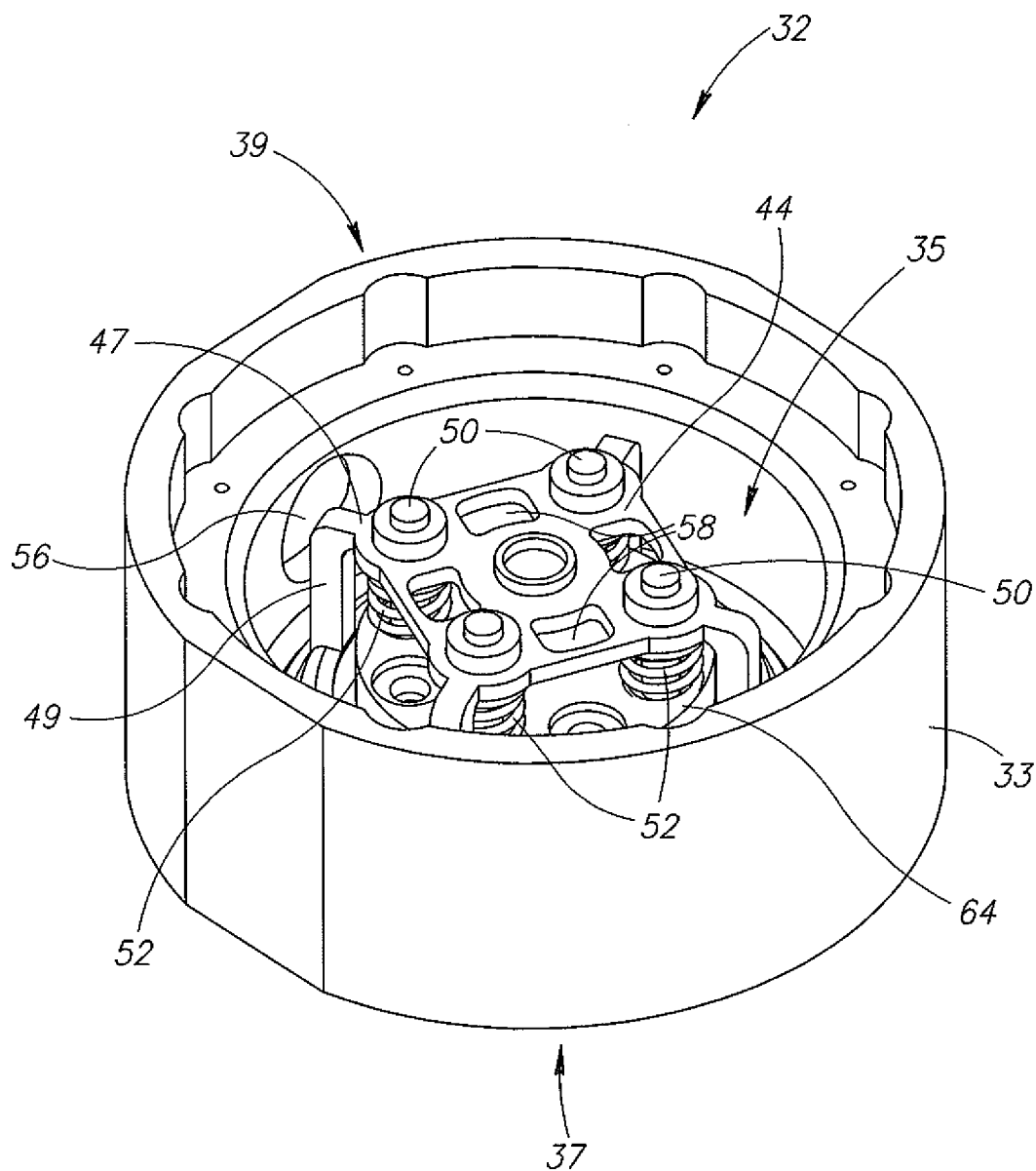
FIG. 6 is a perspective illustration of an internal view of a portion of a shutter assembly, in accordance with embodiments of the present invention.

Reference is now made to FIG. 6, which is a perspective illustration of an internal view of a portion of shutter assembly 32, in accordance with embodiments of the present invention. Shutter assembly 32 includes a shutter assembly housing 33 defining a chamber 35. Chamber 35 is a portion of cavity 24 of respiration module 12, described above with reference to FIG. 1. However, chamber 35 refers to the portion of cavity 24 which is part of shutter assembly 32. Chamber 35 has a proximal end 37, which is the end closest to mouthpiece 30 when mouthpiece is present and which is proximal to movable portion 44 of shutter assembly 32, and a distal end 39, which is distal to movable portion 44 and which is closed to air flow. Thus, air flows from proximal end 37 to distal end 39, but is configured to exit chamber 35 via an outlet 56 positioned along a wall of chamber 35. A fixed portion 64 is positioned at proximal end 37 of chamber 35. Movable portion 44 includes a flat surface 47, a sealing portion 60 (not shown) and a connecting portion 54 connecting flat surface 47 to sealing portion. Movable portion 44 is positioned adjacent to and is movable with respect to fixed portion 64 via leading pins 50 and springs 52 positioned there between.

Figure 7A:
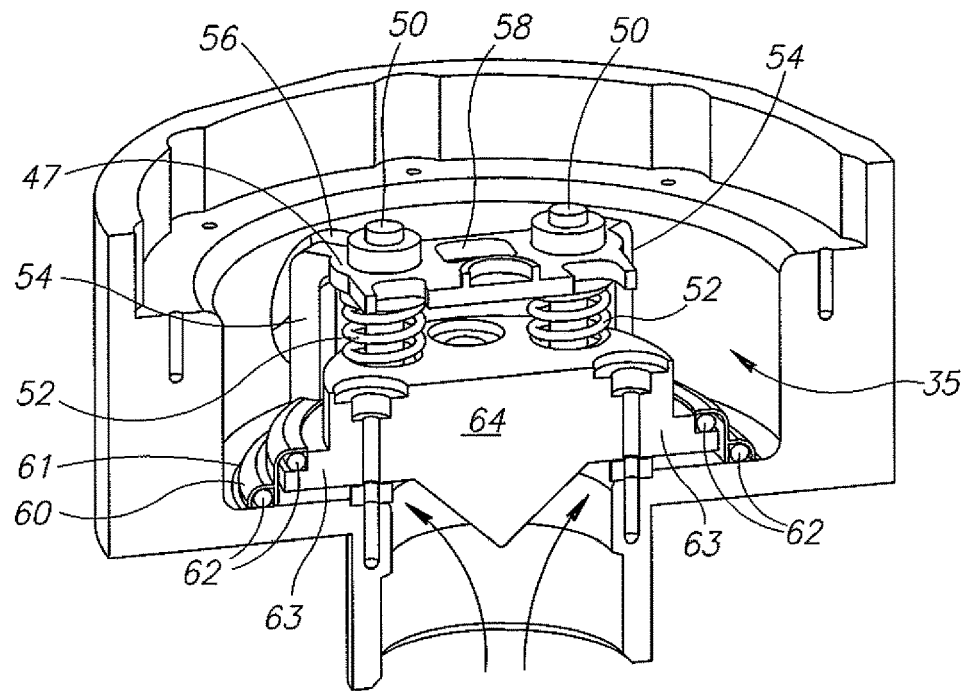
FIG. 7A and FIG. 7B are partially cut-away perspective illustrations of the shutter assembly of FIG. 6, shown in a sealed configuration and an open configuration, respectively.
Figure 7B:
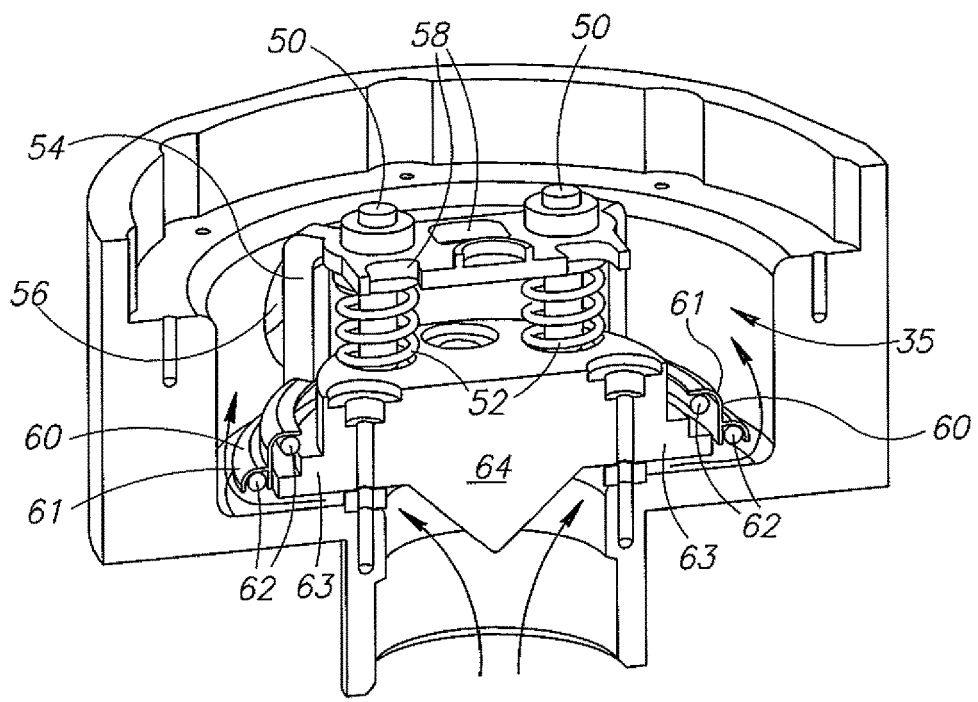

Reference is now made to FIG. 7A and FIG. 7B, which are partially cut-away perspective illustrations of shutter assembly 32 in a sealed configuration and an open configuration, respectively. As shown in FIG. 7A, sealing portion 60 of movable portion 44 includes a circular compartment 61 within which may be positioned a set of O-rings 62. One of O-rings 62 may be positioned against a chamber floor and the other one of O-rings 62 may be positioned against a stair 63 of fixed portion 64. When movable portion 44 is pushed towards fixed portion 64 (via motor 34 such as a solenoid, for example) as shown in FIG. 7A, circular compartment 61 fully encloses O-rings 62, thus preventing air flow. When movable portion 44 is released, springs 52 push movable portion 44 away from fixed portion 64, resulting in air space between O-rings 62 and the chamber floor. Thus, air can flow into chamber 35, and out through outlet 56 located on a wall of chamber 35. It is a feature of the present invention that the shutter assembly allows for minimal air displacement. This may be accomplished, for example, by providing a small area of movement which can be used to displace a large amount of air and which has available a large "flow area", defined as an area available for air flow. In the present example, this feature can be seen as follows. The area through which air flows is the area of sealing in the vicinity of the O-rings, and is substantially proportional to the circumference of the O-rings. Moreover, since flat surface 47 is full of openings 58, movement of movable portion 44 has a relatively small surface area. Thus, movements are contained to a small surface area, while allowing for a relatively large flow area in a post-shutter component of cavity 24.

Figure 8A:
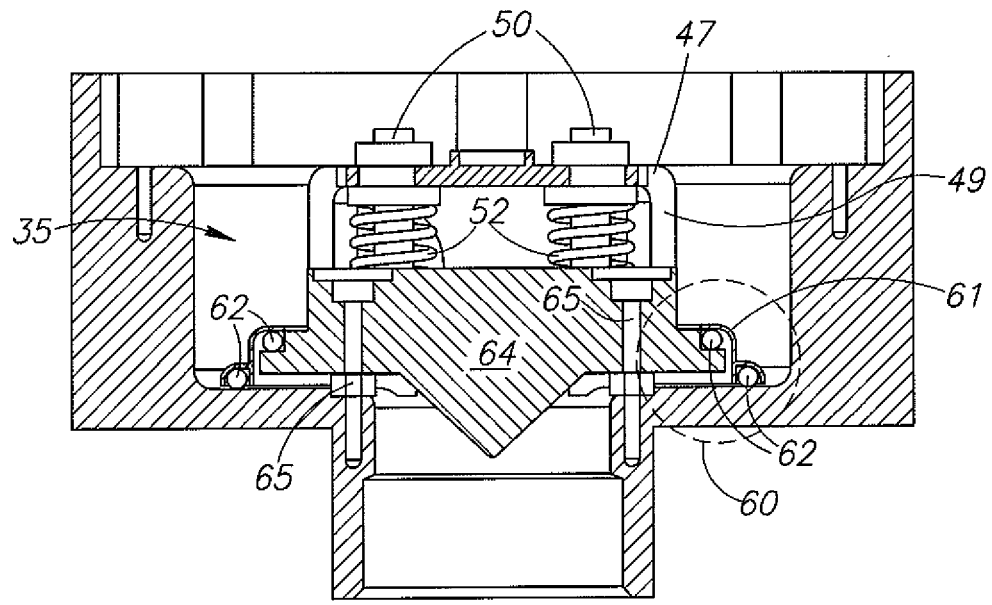
FIG. 8A is a cross sectional illustration of a chamber of the shutter assembly of FIG. 6.
Figure 8B:
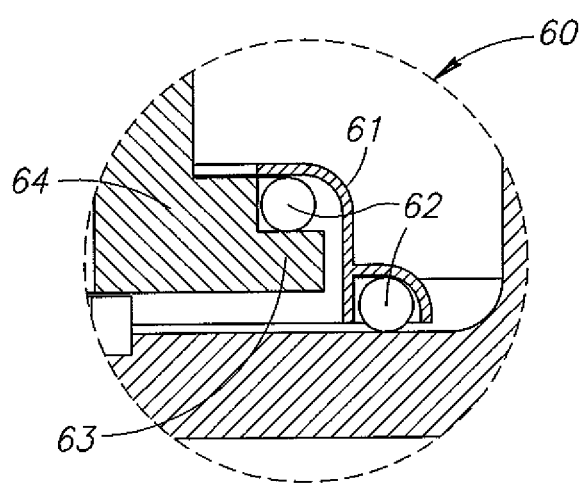
FIG. 8B is a cross sectional illustration showing a sealing portion of the shutter assembly of FIG. 8A in greater detail.

Reference is now made to FIG. 8A, which is a cross sectional illustration of chamber 35 of shutter assembly 32. Fixed portion 64 is fixed to chamber 35 via screws 65 or other fixation means. Flat portion 47, connecting portion 54 and sealing portion 60 of movable portion 44 are all visible in cross section. Springs 52 positioned on pins 50 allow for movement of movable portion 44 with respect to fixed portion 64. Reference is now made to FIG. 8B, which is a cross sectional illustration showing sealing portion 60 in greater detail. Sealing portion 60 includes circular compartment 61 with O-rings 62 positioned therein. O-rings 62 are positioned on fixed portion 64 and on the floor of chamber 35.

Figure 9A:
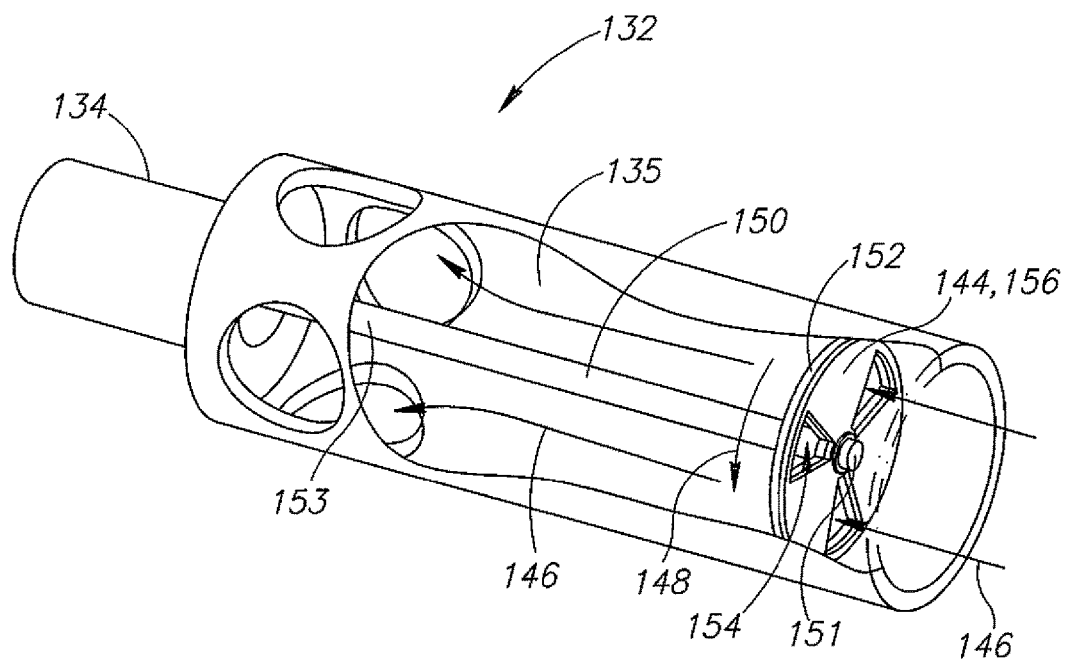
FIG. 9A is a perspective illustration of a shutter assembly in accordance with additional embodiments of the present invention.

Reference is now made to FIG. 9A, which is a perspective illustration of a shutter assembly 132 in accordance with additional embodiments of the present invention. Shutter assembly 132 includes a chamber 135 for air flow wherein chamber 135 is substantially cylindrical in shape. A motor 134 is positioned at a first end of chamber 135 and is attached to a rotatable shaft 150 running through a center of chamber 135. Motor 134 is configured to provide rotational movements to rotatable shaft 150. Rotatable shaft 150 includes a proximal end 151 and a distal end 153. Motor 134 may be attached to distal end 153, although other locations are possible as well. Motor 134 may be any motor suitable for providing such movements, such as a step motor, for example. At proximal end 151 of rotatable shaft 150, there is positioned a disk 152 having openings 154 for air flow. Disk 152 fits within chamber 135 such that air cannot flow around the sides of disk 152, but can only flow through openings 154. A movable portion 144 comprises a rotating shutter 156 attached to proximal end 151 of rotatable shaft 152 and is configured to rotate upon activation of motor 134.

Rotation of rotating shutter 156 causes openings 154 to be closed, thus blocking air flow. A direction of air flow, shown by arrows 146 is substantially orthogonal to a direction of rotation of rotating shutter 156, depicted by arrow 148. Moreover, a cross-sectional surface area of movable portion 144 in the direction of movement of movable portion 144 is equivalent to the thickness of the rotating disk, since movement occurs in the rotational plane. This surface area is much smaller than the flow area just past rotating shutter 156. In one embodiment, disk 152 may be rotatable in a direction opposite to the rotation of rotating shutter 156. This provides faster shuttering speeds than one moving part.

Figure 9B:
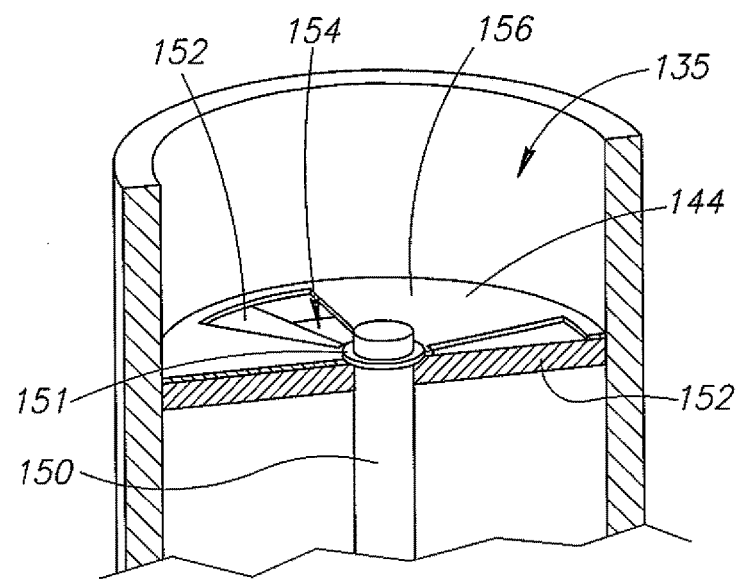
FIG. 9B is a partially cut away view of the shutter assembly of FIG. 9A.

Reference is now made to FIG. 9B, which is a partially cut away view of disk 152, openings 154, and movable portion 144—which is rotating shutter 156.

Figure 10:
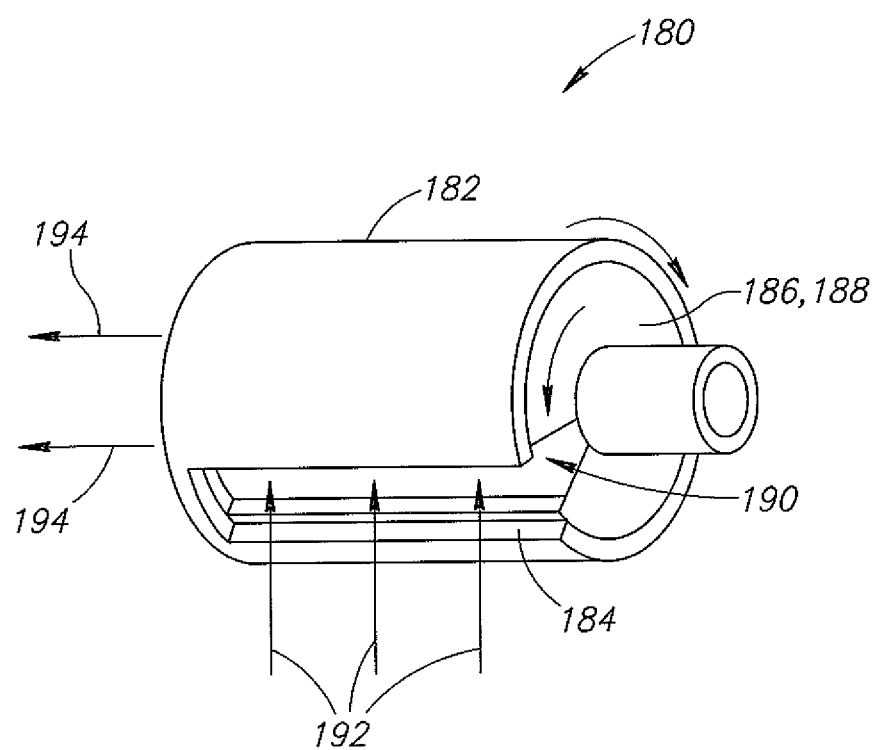
FIG. 10 is a perspective illustration of a shutter assembly in accordance with yet additional embodiments of the present invention.

Reference is now made to FIG. 10, which is a perspective illustration of a shutter assembly 180, in accordance with yet additional embodiments of the present invention. Shutter assembly 180 includes an outer cylinder 182 with an outer slit 184 along at least a portion of a length thereof. Outer slit 184 is preferably long and narrow. A movable portion 186 includes an inner rotatable cylinder 188 having an inner slit 190 along at least a portion of a length thereof. Inner rotatable cylinder 188 is positioned within said outer cylinder 182 such that air is prevented from flowing between outer cylinder 182 and inner rotatable cylinder 188. When outer slit 184 and inner slit 190 are aligned, an opening is created for movement of air flow in a direction of arrows 192 and arrows 194. Inner rotatable cylinder 188 rotates in one direction. In some embodiments, outer cylinder 182 may rotate as well, in an opposite direction of inner rotatable cylinder 188. This provides faster shuttering speeds than one moving part.

In addition, the shape of inner slit 190 and outer slit 184 may be configured so as to minimize shuttering time while maximizing air flow. For this reason, a rectangular shape may be used, wherein a narrow width allows for rapid opening and closing, while the length provides a relatively large flow area.

Methods of Calculation:

The basic concept of the methods of the present invention is that estimation of RV, TLC and TGV may be done based on measurements of the change of volume of gas in the lungs, $\Delta V$, and the accompanying pressure change in the lungs, $\Delta P$, during a short interruption to the breathing of the patient. The interruption is achieved by a quick shutter that shuts the mouth of the patient for a short period of time, either during exhalation or during inhalation. Devices which may be used for quick shuttering with minimal air displacement which may be used in the methods of the present invention are described above with reference to FIGS. 1-10. Quick shuttering is critical in order to obtain resolution necessary to discern parameters which may be measured to obtain volume values.

The first parameter which must be obtained is $V_0$, the instantaneous volume of gas in the lungs at a given point in time. For the purposes of the present invention, $V_0$ is taken as the volume of gas within the lungs upon the shutter event. $V_0$ may be obtained in many different ways. Two different methods for obtaining $V_0$ are described hereinbelow as Method A and Method B. Once $V_0$ is obtained, the following method may be used to obtain TGV.

Figure 11:
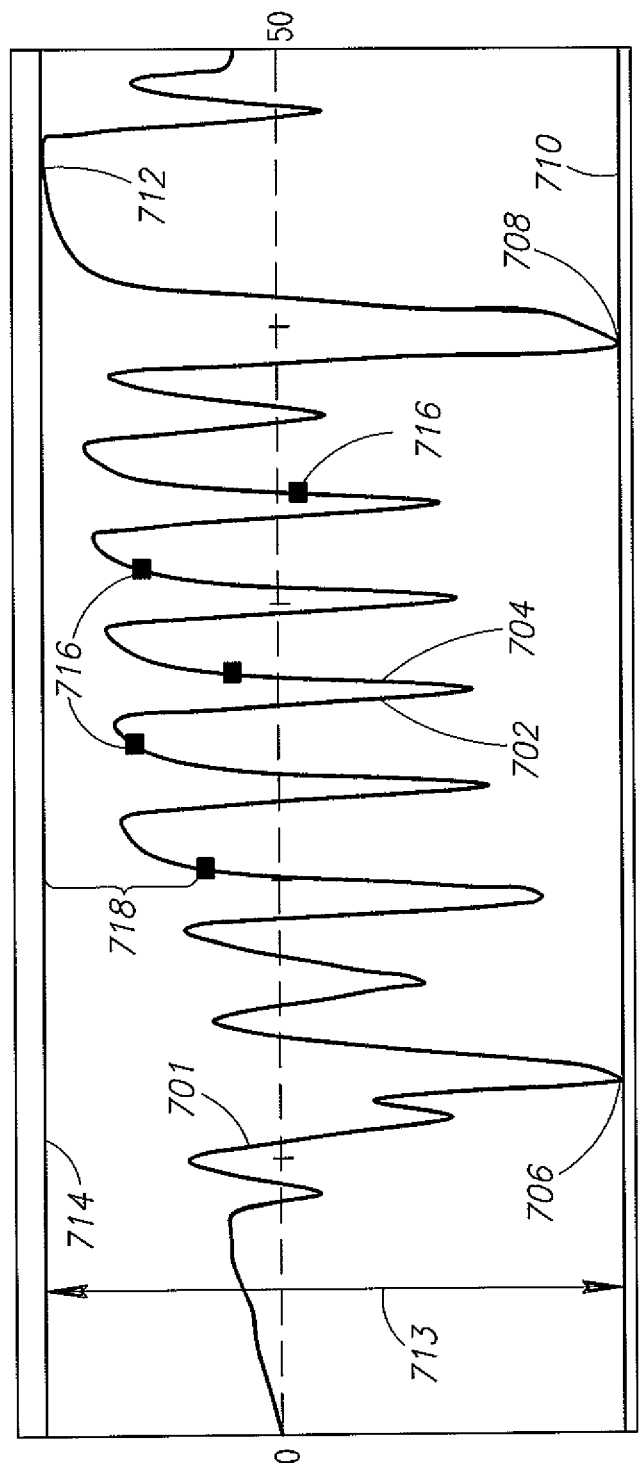
FIG. 11 is a graphical illustration showing volume changes over the course of a series of inspirations and expirations.

Reference is now made to FIG. 11, which is a graphical illustration showing a volume curve 701 over the course of a series of inspirations and expirations, which are not necessarily tidal respirations. Inspirations 702 are shown on the curve going from top to bottom, and expirations 704 are shown going from bottom to top. TLC is determined by a first full inspiration 706 and a second full inspiration 708 taken to full capacity. Thus, a patient is asked to fully inhale at least twice in each session in order to determine TLC level 710, preferably at the beginning and at the end of each measurement session, to account for potential drifting of volume along the series of inspirations and expirations exercised by the subject. TLC level 710 is obtained directly from these two full inspirations. Following second full inspiration 708, the patient is asked to exhale fully in order to obtain a full expiration 712. RV level 714 is obtained directly from full expiration 712, and in parallel to TLC level 710. The amplitude from RV level 714 to TLC level 710 equals VC 713.

At several points along the volume curve 701, a shutter event is initiated, and $V_0$ is calculated by one of methods A or B. Shutter events are shown in FIG. 11 as points 716. Each of the shutter events may take place at different points along either an inspiration 702 or expiration 704 cycle. The difference in volume between $V_0$ measured at a shutter event 716 and RV level 714, is $RV_{ADJ}$ 718, as computed at that specific timing. $RV_{ADJ}$ 718 stands for all of the volume of air that a subject would have maximally expired during a cycle should the subject have been asked to maximally expire. Thus, once $V_0$ is calculated by one of methods A or B per a single shutter event 716, RV is obtained as follows:

$$RV = V_0 - RV_{ADJ}$$

$RV_{ADJ}$ 718 may be large or small depending on when the shutter event is initiated. However, it is necessarily smaller than VC 713, which equals the difference between TLC level 710 and RV level 714. Once RV has been calculated, TLC can be obtained as follows:

$$TLC = RV + VC$$

and TGV can be obtained by:

$$TGV = RV + ERV$$

where ERV (Expiratory Reserve Volume), is obtained by a standard spirometry measurement.

Methods A and B for determination of $V_0$ will now be described.

Method A:

Starting from the ideal gas law $$PV = nkT$$

where P is the pressure, V the volume, n the number of gas molecules and T the gas temperature, we obtain for the gas in the lungs which is maintained at a fixed temperature (also known as Boyle's Law)

$$P_0 V_0 = \text{Const.}$$

If the lungs contract by some volume $\Delta V$, then the pressure in the lungs rises by an amount $\Delta P$, so that $$P_0 V_0 = (V_0 - \Delta V)(P_0 + \Delta P)$$

which yields, $$V_0 = \Delta V / \Delta P (P_0 + \Delta P)$$

If the changes in volume and pressure are small compared to the absolute values $V_0$ and $P_0$, $$V_0 = P_0 \frac{\Delta V}{\Delta P}$$

Hence, by measuring the change in lung volume and the change in the pressure inside the lungs, and knowing the base pressure—which approximates the atmospheric pressure—the internal volume of the lungs at the moment of shutting, $V_0$, may be extracted.

Figure 12:
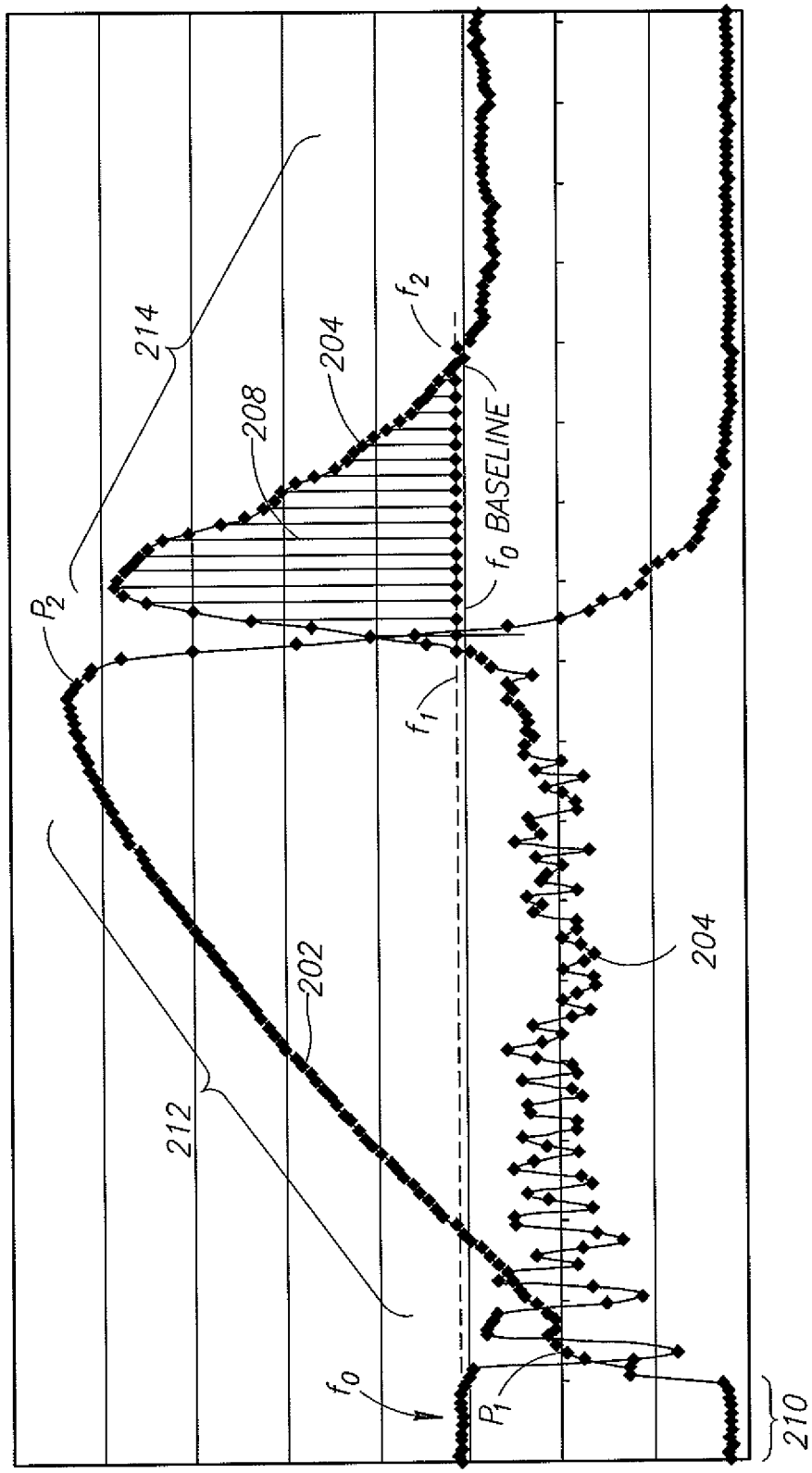
FIG. 12 is a graphical illustration of flow and pressure curves over time obtained during exhalation with a shutter closing episode, showing features used in a method of calculating $V_0$ in accordance with embodiments of the present invention.

Reference is now made to FIG. 12, which is a graphical illustration of flow and pressure curves over time obtained during exhalation with a shutter closing episode. It should be readily apparent that the scale of FIG. 12 is much smaller than the scale of FIG. 11, as FIG. 12 is a depiction of one single shutter event 716 as it relates to FIG. 11. A pre-shutter period 210 is followed by a shutter event 212, which is followed by a post-shutter period 214. Pressure is shown on the upper curve 202 and flow is shown on lower curve 204. Flow decreases to zero during shutter event 212, then rises again, and forms an "overshoot" which relaxes back to the normal flow rate, as the extra volume of gas that was compressed in the lungs during the shutter event is exhaled. The pressure rises sharply when the shutter is closed and then may rise further to a peak just before the shutter opens. Also apparent in FIG. 12 is that during shutter event 212, a small amount of air (compared to $\Delta V$) may escape through the shutter because of less than ideal shutting. This amount of air, referred to as the Escaped Volume and denoted as $\Delta V_{Esc}$ is readily calculated by integrating the flow over shutter event 212. The correction that the escaped volume introduces into the formula for calculating $V_0$ $$V_0 = P_0 \frac{\Delta V - \Delta V_{Esc}}{\Delta P}.$$

A method for determining $V_0$, in accordance with an embodiment of the present invention is described. According to this method, referred to herein as method A, the change in pressure ($\Delta P=P_2-P_1$) is measured during the shutter event (i.e. during the time the shutter is closed), and the change in volume ($\Delta V$) is measured after the shutter is opened. According to this method, the accumulated gas which generates the pressure rise during the shutting is released and measured after the shutter opens. Thus, it is important to quantify the volume which is released due to the shutter event only, and to distinguish this released volume from the volume changes which occur due to regular expiration.

Figure 13:
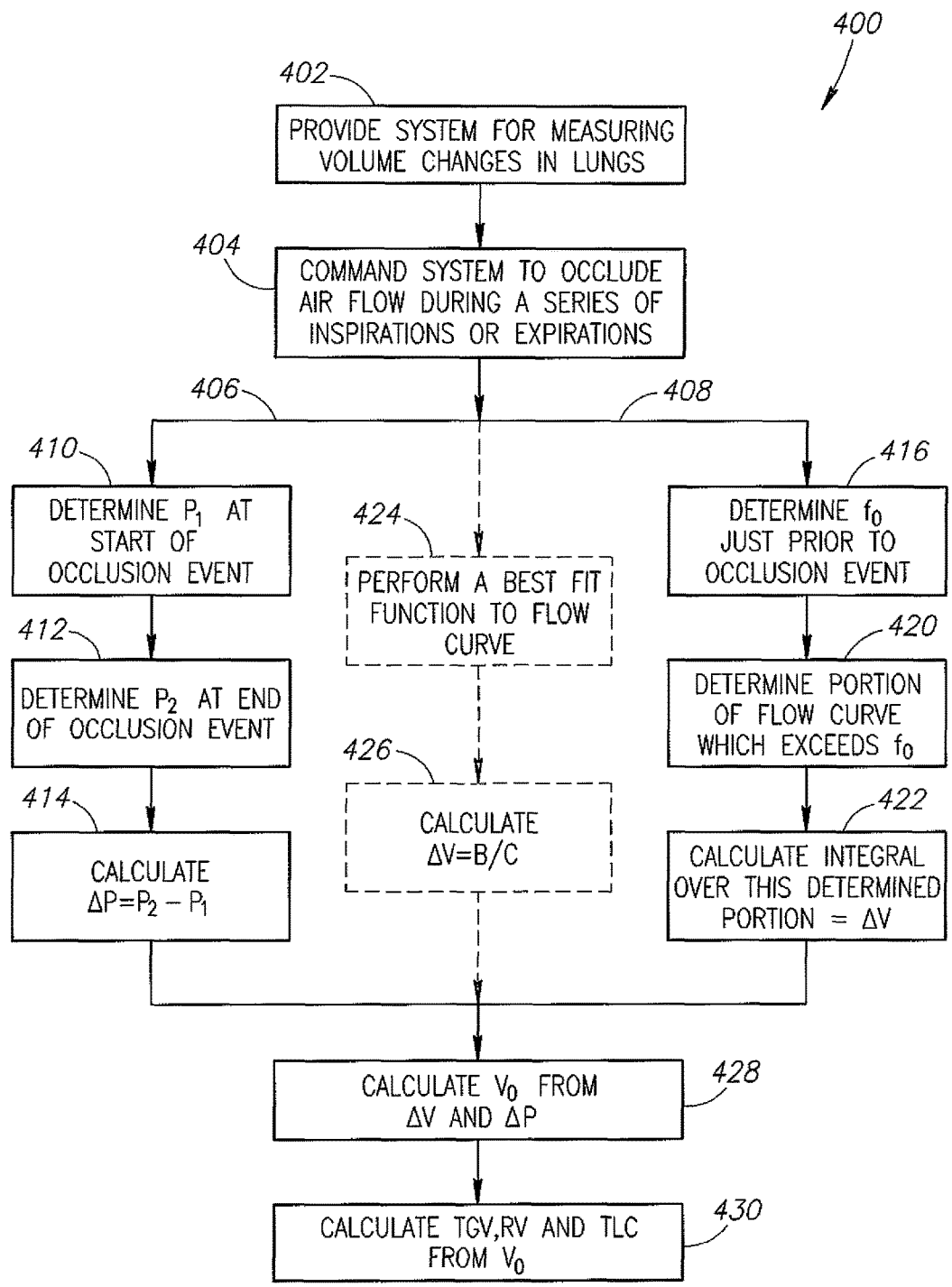
FIG. 13 is a flow chart diagram illustration of the method of FIG. 12 and a method of calculating TGV, RV and TLC in accordance with embodiments of the present invention.

Reference is now made to FIG. 13, which is a flow chart diagram illustration of a method 400 of calculating TGV, in accordance with embodiments of the present invention. First, a system for measuring volume changes in the lungs is provided (step 402). The system includes a respiratory module with means to occlude air flow. Next, a command is given (step 404) to the system to occlude air flow within the respiratory module of the system at various stages of inspiration and/or expiration. The command may be given manually or automatically, or as a combination of both. For a given occlusion event, change in pressure ($\Delta P$) during the occlusion event is calculated (step 406) and change in volume ($\Delta V$) due to released volume due to the occlusion event is calculated (step 408).

Calculation of $\Delta P$ can be done as follows. First, a first pressure $P_1$ is determined (step 410), wherein $P_1$ represents the pressure at the beginning of the occlusion event. $P_1$ is generally determined at a point at which the pressure curve has finished its initial sharp slope and begins a more moderate slope following closing of the shutter, also referred hereinafter the "knee region", as to reflect the general shape of the curve at $P_1$. Next, a second pressure $P_2$ is determined (step 412), wherein $P_2$ represents the pressure at the moment at which the shutter starts to open. Next, the difference between second pressure $P_2$ and first pressure $P_1$ is calculated (step 414), resulting in a value for $\Delta P$.

Calculation of $\Delta V$ can be done as follows. First, $f_0$ is determined (step 416), wherein $f_0$ represents the flow just prior to the occlusion event. This can be done by determining an average of flow measurement data over a range of up to 20 ms prior to closing of the shutter or may be measured via one appropriate data point in the flow measurement raw data. Next, the portion of the flow curve which exceeds $f_0$ is determined (step 420). A baseline, referred to as the $f_0$ baseline, is shown in FIG. 12, stretching between $f_1$ and $f_2$. Finally, the integral of the portion of the flow curve determined in step 420 is calculated (step 422), resulting in $\Delta V$, as illustrated in FIG. 12 by the darkened area 208.

In an alternative embodiment, calculation of $\Delta V$ is done by performing (step 424) a best fit of a function, for example, of the form $A+B*\exp(-C*t)$, to the flow curve, over the range that starts at least 5 ms after the shutter opens and the flow curve starts to rise, and ends at most 100 ms after the shutter opens, where t is the time measured at the point in time when the shutter opens and the flow curve starts to rise, and A, B and C are the fit parameters. Then $\Delta V=B/C$ is calculated (step 426). It should be noted that the time period over which measurements are taken may vary depending on shutter event duration or other parameters. It will be appreciated that the invention is not limited to the methods described herein, and that any method which calculates an excess of air which is exhaled immediately following the opening of the shutter is included within the scope of the present invention. Moreover, the methods of present invention are not dependent on specific shutter event duration parameters. Any parameters which allow for the calculation of the values in accordance with the methods presented herein are within the scope of the present invention.

Once $\Delta V$ and $\Delta P$ are obtained, $V_0$ is calculated (step 428) from $\Delta V$ and $\Delta P$, in accordance with the equation $V_0=(P_0+\Delta P)\Delta V/\Delta P$. Finally, RV, TLC and TGV are calculated (step 430) based on $V_0$, as described above with reference to FIG. 11.

Determination of $P_1$ is critical. However, its exact location may be obscured by oscillations on the pressure signal immediately following shutter closing for as long as 30 ms. In one embodiment, determination of $P_1$ is done by performing an extrapolation of the smooth portion of the pressure signal, backwards to the "knee region", hence overcoming the problem of the oscillations in the immediate vicinity of $P_1$.

Figure 14:
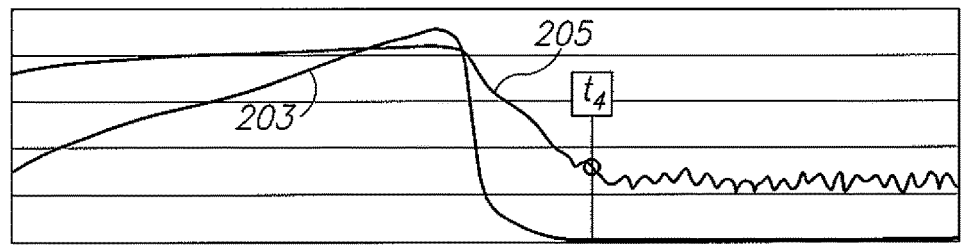
FIG. 14 is a graphical illustration showing a method of measurement of $\Delta V$.

Reference is now made to FIG. 14, which is a graphical illustration showing an alternative measurement of $\Delta V$. According to this method, $\Delta V$ is obtained by integrating the flow curve above the $f_0$ baseline, as described above in FIG. 12. However, the integration is done from the point where the flow crosses $f_0$ when the shutter opens until an identifiable point $t_4$, which is typically different from the point in time when the flow crosses again the level of $f_0$ on its decrease.

The point $t_4$ is identified on the pressure curve, as the point where exponential decrease of the pressure, associated with the relief of excess of air from the lungs, has stopped. This point may be identified by viewing the pressure curve on a logarithmic scale as in FIG. 14, and identifying a knee-shaped pattern on the curve, marked on the graph as $t_4$. In FIG. 14, the pressure curve is shown on a linear scale 203 and on a logarithmic scale 205. The point $t_4$ is marked as the end of the linear decrease of the logarithmic scale 205. It should be noted that the baseline can be varied by assuming that the normal motion of the lungs accelerates linearly from an initial flow rate proportional to $f_0$ to the flow rate at $t_4$.

Example Using Method A:

An example of a measurement taken by measuring $\Delta P$ and $\Delta V$ wherein $\Delta P$ is measured during the time the shutter is closed, and $\Delta V$ is measured during the time the shutter is open, in accordance with method A is now given. In the current example, a patient was requested to inhale fully to the TLC level, and then to immediately exhale fully to the RV level, once at the beginning of the measurement and once at the end of the measurement.

In this example, $RV_{ADJ}$ 718 (FIG. 11)=0.81 L. On pressure curve 202 (FIG. 12) a smooth function is fitted to the curve along the first 50 ms and extrapolated backwards to the point it crosses the pressure curve, $P_1$. $P_2$ is noted at the instant just prior to the opening of the shutter and the sharp decrease of the pressure signal. In this example $P_1$=3.99 mmHg and $P_2$=15.20 mmHg, hence $\Delta P$=11.21 mmHg. The excess volume which is released after the shutter opening $\Delta V$, is the area under the flow curve and above $f_0$ baseline, which in this example stands for $\Delta V$=0.042 L.

From here $V_0$ according to Method A is readily calculated as $$V_{0[A]} = P_0 \frac{\Delta V}{\Delta P} = 760 \frac{0.042}{11.21} = 2.84 \, L$$

Accordingly, RV is found to be $$RV_{[A]} = V_{0[A]} - RV_{ADJ} = 2.84 - 0.81 = 2.03 \, L$$

Method B:

The basic theory behind method B is as follows: Starting from $$P_0 V_0 = \text{Const.},$$

assuming P and V are homogeneous and quasi steady, differentiation over time provides:

$$P_0 \frac{dV}{dt} + V_0 \frac{dP}{dt} = 0$$

where $P_0$ and $V_0$ are the pressure and volume of the system at any given moment. Now dV/dt is the rate of contraction of the lungs' volume, and if we assume continuity of motion over the short period of time of the shutter closing, we conclude that it is equal to the flow rate from the mouth just prior to the closing of the shutter. Hence rearranging the last equation gives $$V_0 = -P_0 \frac{\frac{dV}{dt}}{\frac{dP}{dt}} = \frac{P_0 \cdot f_0}{\frac{dP}{dt}}$$

where $V_0$ is the lungs' volume, $P_0$ approximates the atmospheric pressure, $f_0$ is the flow rate just prior to the shutter closing and dP/dt is the slope of pressure rise (as a function of time) just after the shutter closing.

The rate of change of the volume of the lungs is equal to $f_0$, the flow just prior to the closing of the shutter, and the rate of change of the pressure is measured right after the shutter closes. Assuming continuity in the physical movement of body tissues during breathing, the lungs, which contract at a roughly constant pace during breathing, will continue to contract at the same pace for a short time interval after the shutter closes, and hence contribute to the rise in pressure.

Figure 15:
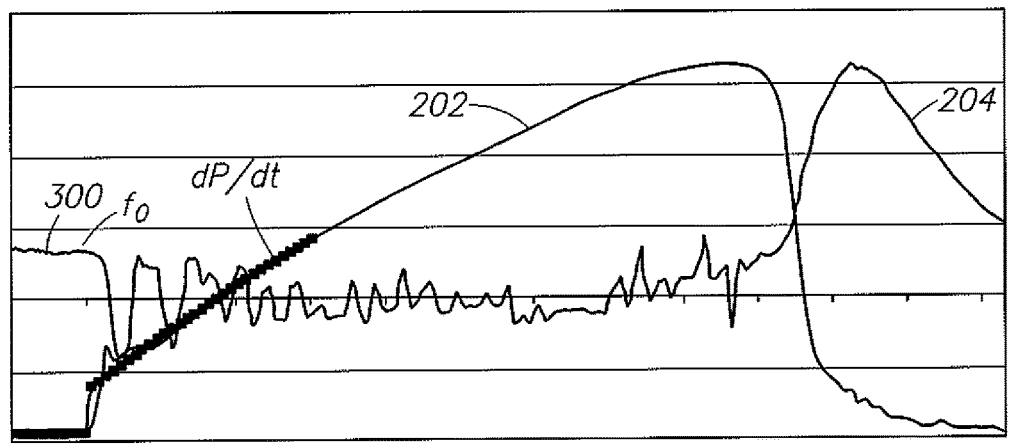
FIG. 15 is a graphical illustration of a flow curve and a pressure curve over time obtained during exhalation with a shutter closing episode, showing features used in another method of calculating $V_0$ in accordance with embodiments of the present invention.

Reference is now made to FIG. 15, which is a graphical illustration of a flow curve 204 and a pressure curve 202 over time obtained during exhalation with a shutter closing episode. According to this method, referred to herein as method B, the rate of change in pressure (dP/dt) is determined during the shutter event (i.e. during the time the shutter is closed), and the instantaneous volume ($V_0$) is calculated rather than obtained by directly measuring a change of volume, $\Delta V$.

Figure 16:
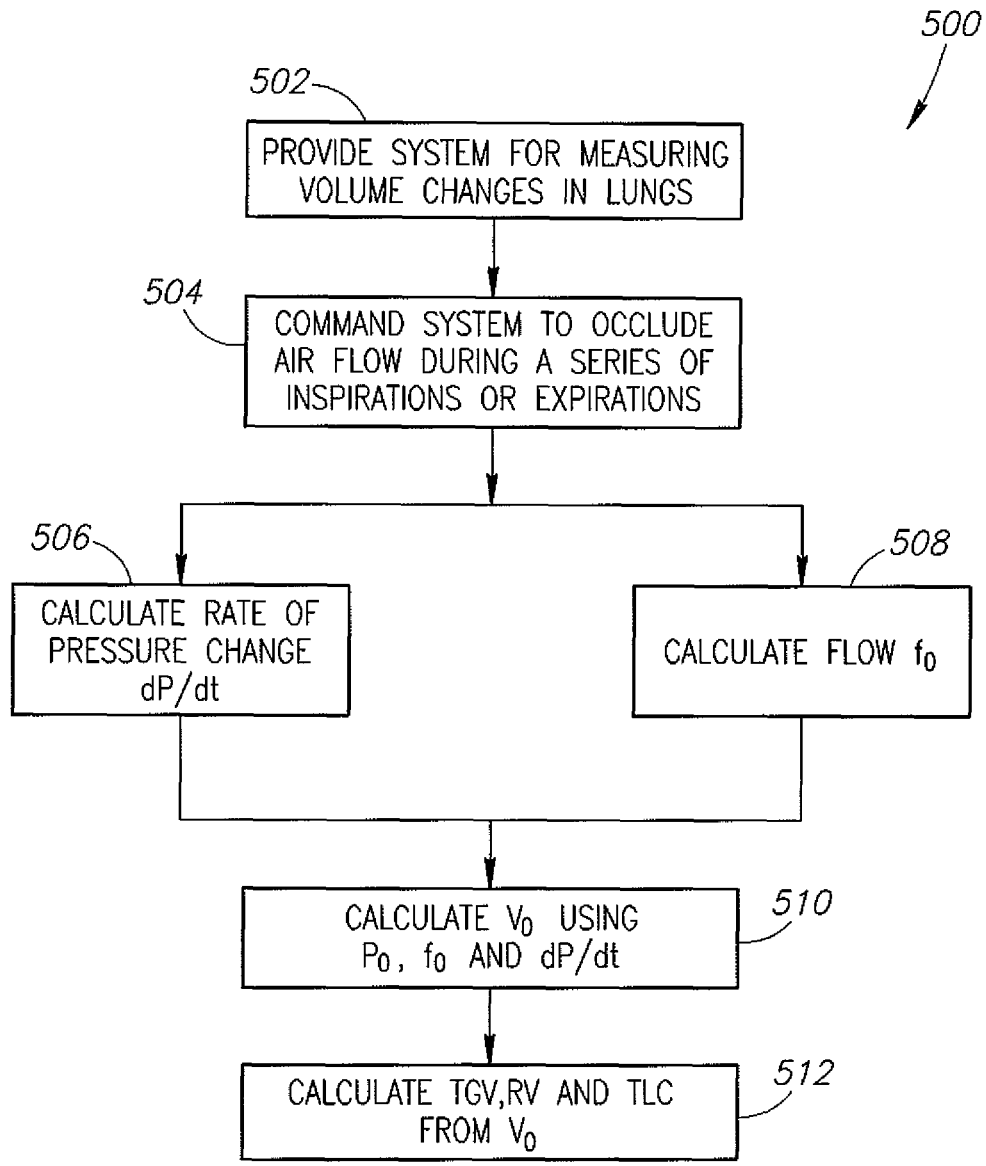
FIG. 16 is a flow chart diagram illustration of the method of FIG. 16 and a method of calculating TGV, RV and TLC in accordance with embodiments of the present invention.

Reference is now made to FIG. 16, which is a flow chart diagram illustration of a method 500 of calculating TGV, RV and TLC in accordance with embodiments of the present invention. First, a system for measuring volume changes in the lungs is provided (step 502). The system includes a respiratory module with means to occlude air flow. Next, a command is given (step 504) to the system to occlude air flow within the respiratory module of the system at various stages of inspiration and/or expiration. The command may be given manually or automatically, or as a combination of both. For a given occlusion event, rate of pressure change (dP/dt) during the occlusion event is calculated (step 506). dP/dt is determined within the first 100 ms following shutter occlusion. During that lapse of time, intrapulmonary pressure generally climbs in comparison to pre-shutter closure level. Rate of volume change (dV/dt) is flow ($f_0$), which is determined (step 508) as described above with reference to Method A. Volume $V_0$ is calculated (step 510) from the equation above, plugging in the values for dP/dt and $f_0$. Finally, TGV, RV and TLC are calculated (step 512) as described above with reference to FIG. 11.

The flow rate $f_0$ is easily determined just prior to the shutter occlusion. However there are a few alternatives for finding the correct slope in the pressure (dP/dt) immediately following the closing of the shutter, without being affected by noise or other disturbances caused by shutter operation. Some of the options are as follows:

1. Measure the slope of the pressure curve (dP/dt) at the very beginning of the pressure rise following shutter occlusion;
2. Measure the slope (dP/dt) after an identifiable point on the pressure curve, which may represent the point of equating the pressure in the lungs to pressure at the mouth;
3. Ignore the first oscillation in the pressure curve and extrapolate backwards the main body of the pressure curve to the beginning of the pressure rise. This extrapolation results in the calculation of the pressure curve slope (dP/dt).

As shown in FIG. 15, the flow rate just prior to the shutting event is determined by the average of the flow rate over approximately 20 ms prior to the shutting event, depicted by line 300. This type of averaging is quite powerful, and even in cases of low flow rates, (around 0.2 L/sec, for example), when the noise may be as high as ±0.05 L/sec, averaging may take the uncertainty down by a factor of ~4.5, namely bring it to around ±5%, which is tolerable.

The slope of the pressure curve (dP/dt) is estimated by fitting a curved smooth function to the pressure curve along the first 30 ms starting at the "knee region". In this way the exact starting point, and any other specific point in this region, does not have a crucial effect on the final result. Hence, the result is relatively unaffected by the exact selection of the fitting range by the operator, or by the existence of the typical oscillation at the "knee region", as long as it is not too large.

As to the fit function, an exponential of the form A−B exp(−C·t) (where A, B and C are the fit parameters) can be used. This function has been found by trial and error as a function that fits to the various shapes that the pressure curve presents in this region. The slope is calculated at the starting point of the curve (namely at t=0) as B·C.

Variations to method B may include, for example, the fitting of any general smooth function to the pressure curve, and estimating the slope at any given point t>$t_0$. For example, the fit function may be of the form:

$$f = A - B \cdot \exp(-C \cdot t) + D \cdot t$$

As one example, the fit range may be changed from 30 ms to 50 ms, and the evaluation of the slope may be done at t=5 ms. The slope is thus given in this example by $$f = B \cdot C \cdot \exp(-C \cdot t) + D |_{t=5}$$

Another variation of Method B may be the fitting of a sinusoidal component to the oscillations, which could help difficulties in fitting a smooth function to the pressure curve when the oscillations on the pressure curve following the shutter closing are large. Thus, the fit function may be of the form $$f = A - B \cdot \exp(-C \cdot t) + D \cdot t + E \cdot \sin(F \cdot t + G)$$

The sinusoidal component then fits to the oscillations, and the smooth component emulates the net slope of the pressure curve. The slope of the smooth portion of the fit function at any point t may be again evaluated by $$f = B \cdot C \cdot \exp(-C \cdot t) + D|_t.$$

Example Using Method B:

Referring again to FIG. 16, to calculate $V_0$ according to Method B we find $f_0$ to be $f_0$=1.22 L/sec. The slope of the interpolated smooth function, estimated 10 ms after the shutter closing (namely after point) to minimize the effects of the oscillations following the shutter closing, is 333 mmHg/sec. According to method B we thus find $$V_{0[B]} = \frac{P_0 F_0}{\frac{dP}{dt}} = 760 \frac{1.22}{333} = 2.78 \text{ L}$$

hence $$RV_{[B]} = V_{0[B]} - RV_{ADJ} = 2.78 - 0.81 = 1.97 \text{ L}$$

To summarize, the examples provided in Method A and Method B provide substantially the same result, which is also in agreement with the measured RV for this individual, which is approximately 2.0 L, measured by body plethysmography. Small differences between the results of the two methods as well as the difference with respect to results using body plethysmography are associated with measurement noise and may be reduced through averaging.

Example with Results

The tables below detail typical results obtained from measurement of a human volunteer. During measurement, the volunteer would breathe normally through the device which was attached to his mouth through a mouthpiece, so as to ensure that there is absolutely no escape of air between the lips and the mouthpiece. A nose clip ensures there is no escape of air through the nose. While breathing, the volunteer holds his hands on his cheeks, to prevent sudden blowing of the cheeks when the shutter closes. The device recorded flow and pressure data continuously.

Each measurement consisted of a series of breathing cycles, while in each exhale portion the shutter was shut momentarily and opened again. In the last breathing cycle the volunteer was asked to exhale forcefully and fully, so that by the end of the last breathing cycle it is assumed the volume of the lungs reaches the volunteer's RV level. During the shutter event the flow signal drops abruptly to zero and the pressure rises sharply as the pressure in the lungs grows.

Table 1 presents results of 6 measurements taken over a period of two weeks. The table compares RV results that were calculated using Method A (presented as $RV_{[A]}$) and RV results that were calculated using Method B (presented as $RV_{[B]}$). The average of all six measurements is compared to the body plethysmograph RV results of the same individual, obtained in accordance with ATS guidelines. VC results measured were in agreement with VC results calculated by a body plethysmograph, and thus, TLC results were in agreement with body plethysmograph's results as well.

TABLE 1

| | 1 | 2 | 3 | 4 | 5 | 6 | average | Body Plethysmograph |
|---|---|---|---|---|---|---|---|---|
| $RV_{[A]}$ | 2.46 | 2.35 | 2.29 | 2.28 | 2.29 | 2.48 | 2.36 | 2.39 |
| $RV_{[B]}$ | 2.17 | 2.41 | 2.43 | 2.15 | 2.20 | 2.45 | 2.30 | 2.39 |

The results shown in the tables above show that there is agreement between the results obtained by the industry standard (ie, body plethysmograph), and the results obtained by the device and method of the present invention. These results show that the device and method of the present invention adequately measure a person's RV, TGV and TLC.

While certain features of the present invention have been illustrated and described herein, many modifications, substitutions, changes, and equivalents may occur to those of ordinary skill in the art. It is, therefore, to be understood that the appended claims are intended to cover all such modifications and changes as fall within the true spirit of the present invention.

The invention claimed is:

1. A method to calculate lung volumes using a respiratory measurement device, comprising:
   providing a respiration module for inhalation or exhalation, including:
   an electric motor,
   a motor-controlled shutter positioned within the respiration module and movable via the electric motor,
   a flow measurement component, and
   a pressure measurement component;
   providing a control unit, including:
   a converter to: (i) convert analog data received from the flow measurement component and the pressure measurement component into a digital format, and (ii) convert digital signals into commands for the electric motor, and
   a processor in electrical communication with the electric motor, the flow measurement component, and the pressure measurement component via the converter;
   commanding, by the processor, the electric motor to occlude air flow with the motor-controlled shutter during an inhalation or exhalation;
   obtaining, by the flow measurement component, a mouth flow curve in at least one of a time duration prior to said occlusion or a time duration subsequent to said occlusion, wherein the processor measures said time duration based at least in part on when the command was provided to the electric motor;

obtaining, by the pressure measurement component, a mouth pressure curve in a time duration during said occlusion, wherein the processor measures said time duration based at least in part on when the command was provided to the electric motor;

calculating a rate of pressure change;

determining a baseline flow prior to said occlusion;

calculating an absolute lung volume during said occlusion based on said rate of pressure change and said baseline flow; and outputting said calculated absolute lung volume for a pulmonary diagnosis.

2. The method of claim 1, wherein said occlusion of air flow is accomplished in one of: (1) less than 25 ms, (2) less than 5 ms, or (3) less than 2 ms.

3. The method of claim 1, wherein obtaining the mouth flow curve comprises:

measuring a plurality of differential pressures between a portion of the respiration module and an ambient environment;

determining, by the processor, a plurality of volumetric flow rates based on the measured plurality of differential pressures; and determining, by the processor, the mouth flow curve based on the determined plurality of volumetric flow rates.

4. The method of claim 1, further comprising:

calculating, by the processor, an additional lung volume parameter based on said calculated absolute volume.

5. The method of claim 4, wherein said additional lung volume parameter comprises at least one of: TGV, FRC, RV or TLC.

6. The method of claim 1, wherein calculating a rate of pressure change comprises at least one of:

calculating said rate of pressure change immediately subsequent to an initiation of said occlusion;

calculating said rate of pressure change within 100 ms subsequent to an initiation of said occlusion;

calculating said rate of pressure change at a beginning of a rise of pressure subsequent to an initiation of said occlusion; or calculating said rate of pressure change at a point in which a lung pressure is equal to a mouth pressure.

7. The method of claim 1, wherein said determined baseline flow comprises a rate of change of lung volume.

8. The method of claim 7, wherein determining a baseline flow prior to said occlusion comprises determining said rate of change of lung volume just prior to said occlusion.

9. The method of claim 8, wherein determining said rate of change of lung volume just prior to said occlusion comprises determining an average rate of change of lung volume over about 20 ms prior to said occlusion.

10. The method of claim 1, wherein calculating a rate of pressure change comprises at least one of:

performing a smooth curve fit to about 30 ms of said mouth pressure curve; performing an exponential curve fit to said mouth pressure curve; or performing a sinusoidal curve fit to said mouth pressure curve.

11. The method of claim 1, wherein calculating said absolute volume based on said rate of pressure change and said baseline flow comprises determining a ratio of said baseline flow to said rate of pressure change.

12. The method of claim 1, wherein the calculated absolute lung volume is associated with a patient and said output from the respiratory measurement device is received by a user, and further comprising:

performing, by the user, the pulmonary diagnosis of the patient.

13. A method to calculate lung volumes using a respiratory measurement device, comprising:

providing a respiration module for inhalation or exhalation, including:

an electric motor, a motor-controlled shutter positioned within the respiration module and movable via the electric motor, a flow measurement component, and a pressure measurement component providing a control unit, including:

a converter to: (i) convert analog data received from the flow measurement component and the pressure measurement component into a digital format, and (ii) convert digital signals into commands for the electric motor, and a processor in electrical communication with the electric motor, the flow measurement component, and the pressure measurement component via the converter;

commanding, by the processor, the electric motor to occlude air flow with the motor-controlled shutter during an inhalation or exhalation;

obtaining, by the flow measurement component, a mouth flow curve in a time duration subsequent to said occlusion, wherein the processor measures said time duration based at least in part on when the command was provided to the electric motor;

obtaining, by the pressure measurement component, a mouth pressure curve in a time duration during said occlusion, wherein the processor measures said time duration based at least in part on when the command was provided to the electric motor;

determining a first pressure at a first point along said mouth pressure curve;

determining a second pressure at a second point along said mouth pressure curve;

calculating a pressure change by calculating a difference between said first pressure and said second pressure;

determining a first flow point along said mouth flow curve, wherein said first flow point is a first point which reaches a baseline flow value following said occlusion of air flow;

determining a second flow point along said mouth flow curve, wherein said second flow point is a second point which reaches said baseline flow value following said first flow point;

calculating a volume change by integrating said flow curve from said first flow point to said second flow point; and calculating an absolute lung volume during said occlusion from said pressure change and said volume change; and outputting said calculated absolute lung volume for a pulmonary diagnosis.

14. The method of claim 13, further comprising; calculating, the processor, an additional lung volume parameter based on said calculated absolute volume.

15. The method of claim 14, wherein said additional lung volume parameter comprises at least one of: TGV, FRC, RV or TLC.

16. The method of claim 13, wherein said occlusion of air flow is accomplished in one of: (1) less than 25 ms, (2) less than 5 ms, or (3) less than 2 ms.

17. The method of claim 13, wherein said first point along said mouth pressure curve is approximately at a start of said occlusion of air flow and said second point along said mouth pressure curve is approximately or exactly at an end of said occlusion of air flow.

18. The method of claim 13, wherein obtaining the mouth flow curve in a time duration subsequent to said occlusion comprises:
   measuring a plurality of differential pressures between a portion of the respiration module and an ambient environment;
   determining, by the processor, a plurality of volumetric flow rates based on the measured plurality of differential pressures; and
   determining, by the processor, the mouth flow curve based on the determined plurality of volumetric flow rates.

19. A method to calculate lung volumes using a respiratory measurement device, comprising:
   providing a respiration module for inhalation or exhalation, including:
      an electric motor,
      a motor-controlled shutter positioned within the respiration module and movable via the electric motor,
      a flow measurement component, and
      a pressure measurement component;
   providing a control unit, including:
      a converter to: (i) convert analog data received from the flow measurement component and the pressure measurement component into a digital format, and (ii) convert digital signals into commands for the electric motor, and
      a processor in electrical communication with the electric motor, the flow measurement component, and the pressure measurement component via the converter;
   commanding, by the processor, the electric motor to occlude air flow with the motor-controlled shutter during an inhalation or exhalation;
   obtaining, by the flow measurement component, a mouth flow curve in a time duration prior to said occlusion and a time duration subsequent to said occlusion, wherein the processor measures said time duration based at least in part on when the command was provided to the electric motor;
   obtaining, by the pressure measurement component, a mouth pressure curve in a time duration during said occlusion, wherein the processor measures said time duration based at least in part on when the command was provided to the electric motor;
   calculating, by the processor, an absolute volume in the lungs during said occlusion based on parameters of said mouth flow curve and said mouth pressure curve, wherein said calculating an absolute volume in the lungs comprises:
   determining a first pressure at a first point along said mouth pressure curve;
   determining a second pressure at a second point along said mouth pressure curve;
   calculating a pressure change by calculating a difference between said first pressure and said second pressure;
   determining a first flow point along said mouth flow curve, wherein said first flow point is a first point which reaches a baseline flow value following said occlusion of air flow;
   determining a second flow point along said mouth flow curve, wherein said second flow point is a second point which reaches said baseline flow value following said first flow point;
   calculating a volume change by integrating said flow curve from said first flow point to said second flow point; and
   calculating an absolute volume during said occlusion from said pressure change and said volume change; and
   outputting said calculated absolute lung volume for a pulmonary diagnosis.

20. The method of claim 19, further comprising:
   calculating, by the processor, an additional lung volume parameter based on said calculated absolute volume.

21. The method of claim 20, wherein said additional lung volume parameter comprises at least one of: TGV, FRC, RV or TLC.

22. The method of claim 19, wherein said occlusion of air flow is accomplished in one of: (1) less than 25 ms, (2) less than 5 ms, or (3) less than 2 ms.

23. The method of claim 19, wherein said first point along said mouth pressure curve is approximately at a start of said occlusion of air flow and said second point along said mouth pressure curve is approximately or exactly at an end of said occlusion of air flow.

24. The method of claim 19, wherein obtaining the mouth flow curve in a time duration prior to said occlusion and a time duration subsequent to said occlusion comprises:
   measuring a plurality of differential pressures between a portion of the respiration module and an ambient environment;
   determining, by the processor, a plurality of volumetric flow rates based on the measured plurality of differential pressures; and
   determining, by the processor, the mouth flow curve based on the determined plurality of volumetric flow rates.

25. The method of claim 19, wherein obtaining the mouth flow curve in a time duration prior to said occlusion comprises determining a baseline flow that comprises a rate of change of lung volume.

26. The method of claim 25, wherein determining a baseline flow that comprises a rate of change of lung volume comprises determining said rate of change of lung volume just prior to said occlusion.

27. The method of claim 26, wherein determining said rate of change of lung volume just prior to said occlusion comprises determining an average rate of change of lung volume over about 20 ms prior to said occlusion.

28. A method to calculate lung volumes using a respiratory measurement device, comprising:
   providing a respiration module for inhalation or exhalation, including:
      an electric motor,
      a motor-controlled shutter positioned within the respiration module and movable via the electric motor,
      a flow measurement component, and
      a pressure measurement component;
   providing a control unit, including:
      a converter to: (i) convert analog data received from the flow measurement component and the pressure measurement component into a digital format, and (ii) convert digital signals into commands for the electric motor, and
      a processor in electrical communication with the electric motor, the flow measurement component, and the pressure measurement component via the converter;

commanding, by the processor, the electric motor to occlude air flow with the motor-controlled shutter during an inhalation or exhalation;

obtaining, by the flow measurement component, a mouth flow curve in a time duration subsequent to said occlusion, wherein the processor measures said time duration based at least in part on when the command was provided to the electric motor;

obtaining, by the pressure measurement component, a mouth pressure curve in a time duration during said occlusion, wherein the processor measures said time duration based at least in part on when the command was provided to the electric motor;

determining a first pressure at a first point along said mouth pressure curve;

determining a second pressure at a second point along said mouth pressure curve;

calculating a pressure change by calculating a difference between said first pressure and said second pressure;

determining a first flow point along said mouth flow curve, wherein said first flow point is a first point which reaches a baseline flow value following said occlusion of air flow;

determining a second flow point along said mouth flow curve, wherein said second flow point is substantially equivalent in time to a point along said pressure curve at a local minimum of pressure;

calculating a volume change by integrating said flow curve from said first flow point to said second flow point; and calculating an absolute lung volume from said pressure change and said volume change; and outputting said calculated absolute lung volume for a pulmonary diagnosis.

29. The method of claim 28, further comprising:
calculating, by the processor, an additional lung volume parameter based on said calculated absolute volume.

30. The method of claim 29, wherein said additional lung volume parameter comprises at least one of: TGV, FRC, RV or TLC.

31. The method of claim 28, wherein said occlusion of air flow is accomplished in one of: (1) less than 25 ms, (2) less than 5 ms, or (3) less than 2 ms.

32. The method of claim 28, wherein obtaining the mouth flow curve in a time duration subsequent to said occlusion comprises:
measuring a plurality of differential pressures between a portion of the respiration module and an ambient environment;
determining, by the processor, a plurality of volumetric flow rates based on the measured plurality of differential pressures; and
determining, by the processor, the mouth flow curve based on the determined plurality of volumetric flow rates.

33. The method of claim 28, wherein said first point along said pressure curve is approximately at a start of said occlusion of air flow and said second point along said pressure curve is approximately or exactly at an end of said occlusion of air flow.

34. A method to calculate lung volumes using a respiratory measurement device, comprising:
providing a respiration module for inhalation or exhalation, including:
an electric motor,
a motor-controlled shutter positioned within the respiration module and movable via the electric motor,
a flow measurement component, and
a pressure measurement component
providing a control unit, including:
a converter to: (i) convert analog data received from the flow measurement component and the pressure measurement component into a digital format, and (ii) convert digital signals into commands for the electric motor, and
a processor in electrical communication with the electric motor, the flow measurement component, and the pressure measurement component via the converter;
commanding, by the processor, the electric motor to occlude air flow with the motor-controlled shutter during an inhalation or exhalation;
obtaining, by the flow measurement component, a mouth flow curve in a time duration prior to said occlusion and a time duration subsequent to said occlusion, wherein the processor measures said time duration based at least in part on when the command was provided to the electric motor;
obtaining, by the processor with a pressure measurement component of said device, a mouth pressure curve in a time duration during said occlusion, wherein the processor measures said time duration based at least in part on when the command was provided to the electric motor;
determining a first pressure at a first point along said mouth pressure curve;
determining a second pressure at a second point along said mouth pressure curve;
calculating a pressure change by calculating a difference between said first pressure and said second pressure;
determining a first flow point along said mouth flow curve, wherein said first flow point is a first point which reaches a baseline flow value following said occlusion of air flow;
determining a second flow point along said mouth flow curve, wherein second flow point is substantially equivalent in time to a point along said pressure curve at a local minimum of pressure;
calculating a volume change by integrating said flow curve from said first flow point to said second flow point; and
calculating an absolute lung volume from said pressure change and said volume change; and
outputting said calculated absolute lung volume for a pulmonary diagnosis.

35. The method of claim 34, further comprising:
calculating, by the processor, an additional lung volume parameter based on said calculated absolute volume.

36. The method of claim 35, wherein said additional lung volume parameter comprises at least one of: TGV, FRC, RV or TLC.

37. The method of claim 34, wherein said occlusion of air flow is accomplished in one of: (1) less than 25 ms, (2) less than 5 ms, or (3) less than 2 ms.

38. The method of claim 34, wherein obtaining the mouth flow curve in a time duration prior to said occlusion and a time duration subsequent to said occlusion comprises:
measuring a plurality of differential pressures between a portion of the respiration module and an ambient environment;
determining, by the processor, a plurality of volumetric flow rates based on the measured plurality of differential pressures; and
determining, by the processor, the mouth flow curve based on the determined plurality of volumetric flow rates.

39. The method of claim 34, wherein obtaining the mouth flow curve in a time duration prior to said occlusion comprises determining a baseline flow that comprises a rate of change of lung volume.

40. The method of claim 39, wherein determining a baseline flow that comprises a rate of change of lung volume comprises determining said rate of change of lung volume just prior to said occlusion.

41. The method of claim 40, wherein determining said rate of change of lung volume just prior to said occlusion comprises determining an average rate of change of lung volume over about 20 ms prior to said occlusion.

42. The method of claim 34, wherein said first point along said mouth pressure curve is approximately at a start of said occlusion of air flow and said second point along said mouth pressure curve is approximately or exactly at an end of said occlusion of air flow.

43. A method to calculate lung volumes using a respiratory measurement device, comprising:
- providing a respiration module for inhalation or exhalation, including:
  - an electric motor,
  - a motor-controlled shutter positioned within the respiration module and movable via the electric motor,
  - a flow measurement component, and
  - a pressure measurement component;
- providing a control unit, including:
  - a converter to: (i) convert analog data received from the flow measurement component and the pressure measurement component into a digital format, and (ii) convert digital signals into commands for the electric motor, and
  - a processor in electrical communication with the electric motor, the flow measurement component, and the pressure measurement component via the converter;
- commanding, by the processor, the electric motor to occlude air flow with the motor-controlled shutter during an inhalation or exhalation;
- obtaining, by the flow measurement component, a mouth flow curve in a time duration prior to said occlusion and a time duration subsequent to said occlusion, wherein obtaining a mouth flow curve in a time duration prior to said occlusion comprises determining a baseline flow that comprises a rate of change of lung volume, and determining a baseline flow that comprises a rate of change of lung volume comprises determining said rate of change of lung volume just prior to said occlusion, and determining said rate of change of lung volume just prior to said occlusion comprises determining an average rate of change of lung volume over about 20 ms prior to said occlusion, wherein the processor measures said time duration based at least in part on when the command was provided to the electric motor;
- obtaining, by the pressure measurement component, a mouth pressure curve in a time duration during said occlusion, wherein the processor measures said time duration based at least in part on when the command was provided to the electric motor;
- calculating, by the processor, an absolute lung volume during said occlusion based on parameters of said mouth flow curve and said mouth pressure curve; and
- outputting said calculated absolute lung volume for a pulmonary diagnosis.

* * * * *